US012697365B2

(12) United States Patent
Gokaraju et al.

(10) Patent No.: US 12,697,365 B2
(45) Date of Patent: Aug. 4, 2026

(54) SYNERGISTIC HERBAL COMPOSITIONS FOR IMMUNE BOOSTING AND RESPIRATORY HEALTH

(71) Applicant: LAILA NUTRA PRIVATE LIMITED, Vijayawada (IN)

(72) Inventors: Ganga Raju Gokaraju, Vijayawada (IN); Rama Raju Gokaraju, Vijayawada (IN); Kiran Bhupathiraju, Vijayawada (IN); Venkata Kanaka Ranga Raju Gokaraju, Vijayawada (IN); Trimurtulu Golakoti, Vijayawada (IN); Venkateswarlu Somepalli, Vijayawada (IN); Venkata Krishna Raju Alluri, Vijayawada (IN); Krishanu Senguptha, Vijayawada (IN)

(73) Assignee: LAILA NUTRA PRIVATE LIMITED, Vijayawada (IN)

( * ) Notice: Subject to any disclaimer, the term of this patent is extended or adjusted under 35 U.S.C. 154(b) by 586 days.

(21) Appl. No.: 18/041,467

(22) PCT Filed: Aug. 16, 2021

(86) PCT No.: PCT/IN2021/050784
§ 371 (c)(1),
(2) Date: Feb. 13, 2023

(87) PCT Pub. No.: WO2022/038633
PCT Pub. Date: Feb. 24, 2022

(65) Prior Publication Data

US 2023/0293620 A1 Sep. 21, 2023

(30) Foreign Application Priority Data

Aug. 15, 2020 (IN) ............................ 202041035227

(51) Int. Cl.

| | |
|---|---|
| ***A61K 36/81*** | (2006.01) |
| ***A61K 33/06*** | (2006.01) |
| ***A61K 33/30*** | (2006.01) |
| ***A61K 36/185*** | (2006.01) |
| ***A61K 36/19*** | (2006.01) |
| ***A61K 36/59*** | (2006.01) |
| ***A61P 29/00*** | (2006.01) |
| ***A61P 37/02*** | (2006.01) |

(52) U.S. Cl.
CPC .............. *A61K 36/81* (2013.01); *A61K 33/06* (2013.01); *A61K 33/30* (2013.01); *A61K 36/185* (2013.01); *A61K 36/19* (2013.01); *A61K 36/59* (2013.01); *A61P 29/00* (2018.01); *A61P 37/02* (2018.01)

(58) Field of Classification Search
None
See application file for complete search history.

(56) References Cited

U.S. PATENT DOCUMENTS

| | | | | |
|---|---|---|---|---|
| 10,576,117 | B2 | 3/2020 | Shetty | |
| 2015/0283159 | A1 | 10/2015 | Tatsuda et al. | |
| 2019/0365839 | A1* | 12/2019 | Gokaraju | A61K 36/75 |

FOREIGN PATENT DOCUMENTS

| | | | | |
|---|---|---|---|---|
| WO | 2010/109286 | A1 | 9/2010 | |
| WO | 2013/155175 | A1 | 10/2013 | |
| WO | WO-2017103946 | A2 * | 6/2017 | A61P 35/00 |
| WO | 2017/103946 | A3 | 7/2017 | |
| WO | WO-2018092159 | A1 * | 5/2018 | A61K 36/42 |
| WO | 2018/154602 | A1 | 8/2018 | |

OTHER PUBLICATIONS

International Search Report and Written Opinion for PCT/IN2021/050784 mailed on Dec. 21, 2021.

* cited by examiner

*Primary Examiner* — H. Sarah Park
(74) *Attorney, Agent, or Firm* — Kramer & Amado, P.C.

(57) ABSTRACT

The present invention discloses synergistic herbal compositions comprising a first ingredient *Terminalia chebula* extract containing metal salt or metal complex or metal chelate of at least one phytochemical in the extract selected from chebulagic acid, chebulinic acid, and gallic acid or mixtures thereof; and a second ingredient selected from extract(s), fraction(s), phytochemical(s) or mixtures thereof derived from *Withania somnifera, Tinospora cordifolia* and *Andrographis paniculata*; process for their preparation, methods of treatment and use of such compositions for improving immunity and respiratory health.

20 Claims, No Drawings

SYNERGISTIC HERBAL COMPOSITIONS FOR IMMUNE BOOSTING AND RESPIRATORY HEALTH

TECHNICAL FIELD OF THE INVENTION

The invention relates to synergistic herbal compositions comprising a first ingredient *Terminalia chebula* extract containing metal salt or metal complex or metal chelate of at least one phytochemical in the extract selected from chebulagic acid, chebulinic acid, and gallic acid or mixtures thereof; and a second ingredient selected from extract(s), fraction(s), phytochemical(s) or mixtures thereof derived from *Withania somnifera, Tinospora cordifolia* and *Andrographis paniculata*; process for the preparation of these compositions and methods of improving immunity and respiratory health using these compositions.

BACKGROUND OF THE INVENTION

Immunity: Immunity is the body's natural defense system against various bacterial/viral/fungal infections, and diseases caused due to different environmental stimuli. Primarily, the host immunity is classified into innate and adaptive immune responses. Innate immune responses are rapid and non-specific to pathogens, which are mediated by innate immune cells such as myeloid cells, natural killer (NK) cells, innate lymphoid cells, and humoral systems such as defensins and complement. Adaptive immune responses are slower but specific to the pathogens with the recruitment of B- and T-lymphocytes and generation of long-lived immunological memory. The innate immune system is the first responder within minutes to hours of infection, and in case if the pathogens are not eliminated, adaptive immune mechanisms will be activated with specific recognition and elimination of pathogens. Recent research has clearly demonstrated strong coordinated network between the innate and adaptive immune systems to effectively tackle the infections through bidirectional activation by the amplification of innate immune responses such as phagocytosis and B/T-cell-mediated adaptive immune responses. However, if these immune responses are excessively or inappropriately activated, they can harm host tissues and participate in the development of autoimmune disorders like rheumatoid arthritis, allergies, and cancers.

Many therapeutic effects of plant extracts have been suggested to be due to their wide array of immunomodulatory effects and influence on the immune system of the human body. Phytochemicals such as flavonoids, polysaccharides, lactones, alkaloids, diterpenoids, and glycosides have been reported to be responsible for their immunomodulation properties. Curcumin, for example, is one of the most extensively studied compounds for its immunomodulatory properties. Epigallocatechin-3-gallate, one of the most active and abundant polyphenols of green tea *Camellia sinensis*, has been widely reported for its in vitro and in vivo chemopreventive, anti-angiogenic, anti-invasive, anti-proliferative, anti-inflammatory, and anti-oxidant effects.

Respiratory health: The lungs are constantly exposed to the external environment with the respiratory tract facing daily with 10000 L of inhaled air. Most of the inhaled air contains non-harmful environmental components. However, the lungs are also faced with potential air-borne pathogens, allergens, and environmental pollutants. This constant exposure requires an effective and fast-acting immune system. Hence, the pulmonary immune system contains a broad armamentarium of cellular and humoral defense mechanisms in the airways. The coordinated, complex interplay between the resident airway epithelial cells and infiltrating immune cells with the secretions of defensins, mucins, or collectins shapes the outcome of host-pathogen, host-allergen, host-particle interactions within the airway microenvironment. These interactions will further activate the downstream immune responses through the release of mediators such as chemokines (CCL-2, CCL-20), cytokines (IL-1α, IL-1β), and lipid mediators (eicosanoids/leukotrienes). Conversely, excessive immunological tolerance in the airways may lead to ineffective clearance of infectious agents such as influenza, tuberculosis, respiratory syncytial virus, *Streptococcus pneumoniae*, or coronavirus, which in turn may lead to inflammatory lung disease, bronchitis, pneumonia, and sepsis. Respiratory diseases represent an important cause of morbidity and mortality globally, and deaths due to these diseases are increasing worldwide.

Current synthetic drugs hold no promise in the complete healing of these disorders. In contrast, many targets specific herbal alternatives have been recognized due to properties like bronchodilation, mast cell stabilization, anti-inflammatory, anti-allergic, immune-boosting, immunomodulatory as well as inhibitory action on mediators of inflammation (leukotrienes, cyclooxygenase, cytokines, etc.). Thus there is a need for better herbal formulations having built-in immune-stimulating and inflammation-modulating effects to viral respiratory infections while still helping the immune system cope better with the infections.

Patent application US20150283159A1 disclosed a method for preventing or treating cancer, the method comprising: administering, to an individual, an effective amount of an anticancer agent containing ellagitannin wherein the ellagitannin is selected from geraniin, casuarictin, eugeniin, tellimagrandin I, 1,3-di-O-galloyl-4,6-O-hexahydroxydiphenoyl glucose, strictinin, or any combination thereof.

PCT Publication No WO2013/155175 disclosed an enriched hydrolyzable tannoid blend derived from *Terminalia chebula*. An optimized aqueous extraction method for *T. chebula* is provided to maximize the levels of bioactive hydrolyzable tannoids including chebulagic acid, chebulinic acid and other low molecular weight hydrolyzable tannoids.

PCT Publication No WO/2018/154602 disclosed a formulation for treatment and management of diabetes and related complications comprising: an herbal element comprising of *Salacia chinensis, Gymnema sylvestre, Emblica officinalis, Eugenia jambolana, Curcuma longa, Commiphora mukul* and *Tinospora cordifolia* or their extracts thereof and a mineral element comprising of shilajit and bhasma. Wherein said herb element further comprises at least one herb selected from a group consisting of *Withania somnifera, Terminalia chebula, Terminalia bellerica, Andrographis paniculata, Boerhavia diffusa, Azhadirachta indica, Aristolochia indica, Aegle marmelos, Cyperus rotundus, Hemedesmus indicus, Trichosanthes dioica, Santalum alba, Terminalia arjuna, Woodfordia fruiticosa, Glycerrhiza glabra, Mucuna pruriens, Myrica nagi, Plumbago rosea, Inula racemosa, Zingiber officinalis, Piper longum* and *Piper nigrum* or their extracts thereof.

The screening and isolation of more specific immunomodulatory agents from plant origin possesses the potential to counteract the side effects and high cost of synthetic compounds. Thus, the search for natural products of plant origin as new leads for the development of potent and safe immunostimulant agents is an urgent need.

OBJECTIVE OF THE INVENTION

Therefore, the main object of the present invention is to provide synergistic herbal compositions comprising a first ingredient *Terminalia chebula* extract containing metal salt or metal complex or metal chelate of at least one phytochemical in the extract selected from chebulagic acid, chebulinic acid, and gallic acid or mixtures thereof; wherein the metal is selected from zinc, magnesium, calcium and potassium; and a second ingredient selected from extract(s), fraction(s), phytochemical(s) or mixtures thereof derived from *Withania somnifera, Tinospora cordifolia* and *Andrographis paniculata*; for obtaining at least one health benefit selected from improving immunity/eliciting immune response/rejuvenating the immune system, improving innate immunity, improving adaptive immunity, improving cellular immunity, improving humoral immunity, strengthening the natural defense, improving protection from airway inflammation and microbial infection, preventing viral respiratory infections and improving lung function/health and improving respiratory health.

Another objective of the invention is to provide methods of obtaining at least one health benefit selected from improving immunity/eliciting immune response/rejuvenating the immune system, improving innate immunity, improving adaptive immunity, improving cellular immunity, improving humoral immunity, strengthen natural defense, protecting from airway inflammation and microbial infection, preventing viral respiratory infections, improving lung function/health and improving respiratory health in a human; wherein the method comprises supplementing human with an effective dose of a composition comprising a first ingredient *Terminalia chebula* extract containing metal salt or metal complex or metal chelate of at least one phytochemical in the extract selected from chebulagic acid, chebulinic acid and gallic acid or mixtures thereof; and a second ingredient selected from extract(s), fraction(s), phytochemical(s) or mixtures thereof derived from *Withania somnifera, Tinospora cordifolia* and *Andrographis paniculata*; optionally contains at least one component selected from pharmaceutically or nutraceutically or dietically acceptable excipients, carriers and diluents.

Yet another objective of the invention is to provide the use of a synergistic herbal composition comprising a first ingredient *Terminalia chebula* extract containing metal salt or metal complex or metal chelate of at least one phytochemical in the extract selected from chebulagic acid, chebulinic acid and gallic acid or mixtures thereof; and a second ingredient selected from extract(s), fraction(s), phytochemical(s) or mixtures thereof derived from *Withania somnifera, Tinospora cordifolia* and *Andrographis paniculata*; optionally contains at least one component selected from pharmaceutically or nutraceutically or dietically acceptable excipients, carriers and diluents; for obtaining at least one health benefit selected from improving immunity/elicit immune response/rejuvenating the immune system, improving innate immunity, improving adaptive immunity, improving cellular immunity, improving humoral immunity, strengthen the natural defense, improving protection from airway inflammation and microbial infection, preventing viral respiratory infections and improving lung function/health and improving respiratory health.

SUMMARY OF THE INVENTION

The present invention provides synergistic herbal compositions comprising a first ingredient *Terminalia chebula* extract containing metal salt or metal complex or metal chelate of at least one phytochemical in the extract selected from chebulagic acid, chebulinic acid, and gallic acid or mixtures thereof; wherein the metal is selected from zinc, magnesium, calcium and potassium; and a second ingredient selected from extract(s), fraction(s), phytochemical(s) or mixtures thereof derived from *Withania somnifera, Tinospora cordifolia* and *Andrographis paniculata*; for obtaining at least one health benefit selected from improving immunity/eliciting immune response/rejuvenating the immune system, improving innate immunity, improving adaptive immunity, improving cellular immunity, improving humoral immunity, strengthening the natural defense, improving protection from airway inflammation and microbial infection, preventing viral respiratory infections and improving lung function/health and improving respiratory health.

Another aspect of the invention provides synergistic herbal compositions comprising a first ingredient *Terminalia chebula* extract containing metal salt of at least one phytochemical in the extract selected from chebulagic acid, chebulinic acid, and gallic acid or mixtures thereof; and a second ingredient selected from extract(s), fraction(s), phytochemical(s) or mixtures thereof derived from *Withania somnifera, Tinospora cordifolia* and *Andrographis paniculata*; further containing optionally at least one component selected from pharmaceutically or nutraceutically or dietically acceptable excipients, carriers and diluents.

Another aspect of the invention provides a process for the preparation of the compositions comprising a first ingredient *Terminalia chebula* extract containing metal salt of at least one phytochemical in the extract selected from chebulagic acid, chebulinic acid, and gallic acid or mixtures thereof; and a second ingredient selected from extract(s), fraction(s), phytochemical(s) or mixtures thereof derived from *Withania somnifera, Tinospora cordifolia* and *Andrographis paniculata.*

A further aspect of the invention provides method of obtaining at least one health benefit selected from improving immunity/eliciting immune response/rejuvenating the immune system, improving innate immunity, improving adaptive immunity, improving cellular immunity, improving humoral immunity, strengthen natural defense, improving protection from airway inflammation and microbial infection, preventing viral respiratory infections, improving lung function/health and improving respiratory health in a human; wherein the method comprises supplementing human with an effective dose of a composition comprising a first ingredient *Terminalia chebula* extract containing metal salt or metal complex or metal chelate of at least one phytochemical in the extract selected from chebulagic acid, chebulinic acid and gallic acid or mixtures thereof; and a second ingredient selected from extract(s), fraction(s), phytochemical(s) or mixtures thereof derived from *Withania somnifera, Tinospora cordifolia* and *Andrographis paniculata*; optionally contains at least one component selected from pharmaceutically or nutraceutically or dietically acceptable excipients, carriers and diluents.

Another aspect of the invention provides the use of a synergistic herbal composition comprising a first ingredient *Terminalia chebula* extract containing metal salt of at least one phytochemical in the extract selected from chebulagic acid, chebulinic acid and gallic acid or mixtures thereof; and a second ingredient selected from extract(s), fraction(s), phytochemical(s) or mixtures thereof derived from *Withania somnifera, Tinospora cordifolia* and *Andrographis paniculata*; optionally contains at least one component selected from pharmaceutically or nutraceutically or dietically acceptable excipients, carriers and diluents; for obtaining at least one health benefit selected from improving immunity/elicit immune response/rejuvenating the immune system, improving innate immunity, improving adaptive immunity, improving cellular immunity, improving humoral immunity, strengthen the natural defense, improving protection from airway inflammation and microbial infection, preventing viral respiratory infections and improving lung function/health and improving respiratory health.

DETAILED DESCRIPTION OF THE INVENTION

The invention will now be described in detail in connection with certain preferred and optional embodiments, so that various aspects thereof may be more fully understood and appreciated.

The terms "metal salt", "metal complex" and "metal chelate" described herein are used interchangeably. Thus, the statements "*Terminalia chebula* extract containing metal salt of chebulagic acid and/or chebulinic acid and/or gallic acid"; "*Terminalia chebula* extract containing a metal complex of chebulagic acid and/or chebulinic acid and/or gallic acid"; "*Terminalia chebula* extract containing metal chelate of chebulagic acid and/or chebulinic acid and/or gallic acid"; conveys the same meaning and are interchangeable. The terms "improve", "ameliorate" and "better" as used herein conveys the same meaning and are interchangeable. Unless stated to the contrary, any of the words, "including", "includes", "comprising", and comprises" mean "including without limitation" and shall not be construed to limit any general statement that it follows to the specific or similar items.

Unless specified otherwise, all technical and scientific terms used herein have the same meaning as commonly understood by one of ordinary skill in the art to which this invention belongs.

Source of the herbs used in the invention as follows:

1) *Terminalia chebula* fruit raw material was collected from Mulapadu village, Krishna district, Andhra Pradesh and it was wild.
2) *Withania somnifera* root raw material was collected from Kamalapaadu village, Anantapur district, Andhra Pradesh and it was cultivated.
3) *Tinospora cordifolia* stem raw material was collected from Mulapadu village, Krishna district, Andhra Pradesh and it was wild.
4) *Andrographis paniculata* aerial parts raw material was collected from Mulapadu village, Krishna district, Andhra Pradesh and it was wild.

*Terminalia chebula: T. chebula*, a moderate-sized tree, belongs to family Combretaceae-Indian almond family. It is widely used in traditional medicine not only in India but also in other countries like Asia and Africa. *T. chebula* fruit contains high phenolic content, especially hydrolyzable tannins. Chebulagic acid, chebulinic acid, and gallic acid are the major organic acids present in the fruit extract. The chemical structures of chebulagic acid, chebulinic acid, and gallic acid are shown below. The extracts of *T. chebula*, especially fruits, have been widely investigated for their various pharmacological effects such as antioxidant activity, hepatoprotective, antidiabetic, renoprotective, anti anaphylactic, immune modulator, etc. Ethnomedicinal and traditional uses, pharmacological and safety studies of *T. chebula* demonstrated the therapeutic use of this single herb for various disease conditions.

Chemical structures of chebulgic acid, chebulinic acid and gallic acid.

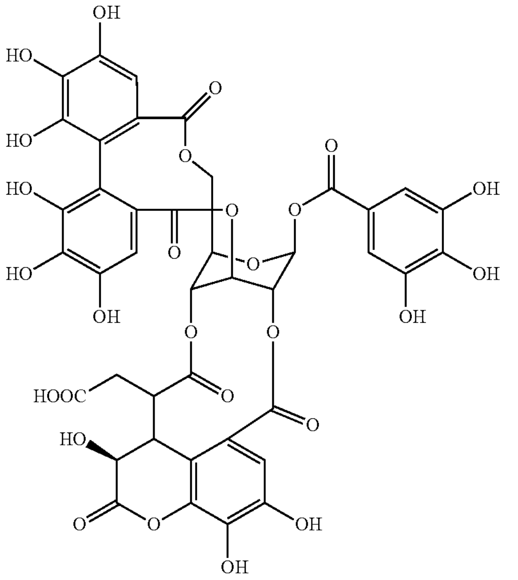

Chebulagic acid

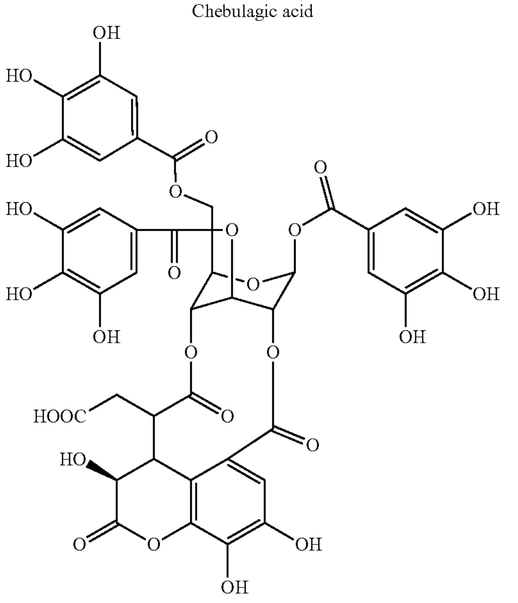

Chebulinic acid

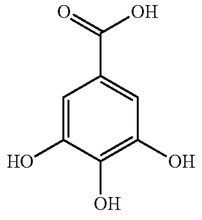

Gallic acid

As estimated, 50% of all drug molecules used in medicinal therapy are administered as salts. The formation of metal salt or metal ion complex of an organic acid is a critical and desirable feature in drug development. The organic acid compounds have specific suboptimal physicochemical or biopharmaceutical properties that can be overcome by pairing the organic acid with a counter metal ion to create a salt or complex form of the compound. This process of metal ion salt or complex is a simple way to modify the properties of an organic acid to overcome undesirable features of the parent compound.

Zinc is the second most abundantly distributed trace element in the body after iron, and its deficiency in humans is now known to be an important malnutrition problem worldwide. Zinc deficiency during growth periods results in growth failure and is a key mineral that cells use to metabolize nutrients. Epidermal, gastrointestinal, central nervous, immune, skeletal, and reproductive systems are the organs most affected clinically by zinc deficiency. Zinc has been clinically reported to be effective in diarrhea, age-related macular degeneration, upper respiratory infections, acne, adjuvant in the treatment of depression, wound healing, etc., and also known to be important in the immune function, DNA and protein production, and cell division. Magnesium, calcium, and potassium are also essential minerals required by the body for various metabolic functions.

The inventors surprisingly found that the *Terminalia chebula* fruit extract containing metal salt of chebulagic acid and/or metal salt of chebulinic acid and/or metal salt of gallic acid; increases water solubility and thus result in improved bioavailability and thereby improve their therapeutic applications such as improving immunity, respiratory health etc.

Therefore, the inventors of the present invention prepared various compositions comprising *Terminalia chebula* extract containing metal salt of at least one phytochemical in the extract selected from chebulagic acid, chebulinic acid and gallic acid or mixtures thereof; and at least one additional ingredient selected from extract, fraction, phytochemical or mixtures thereof derived from *Withania somnifera, Tinospora cordifolia* and *Andrographis paniculata.*

For example, the dried fruits of *T. chebula* were pulverized, and the powder was extracted with 50% aqueous ethanol to obtain 50% aqueous ethanol extract solution. This solution was treated with zinc oxide, and after few hours, the solution was filtered to remove insoluble zinc oxide and concentrated. The dry powder (T.Ch.Zn-1) was estimated for chebulagic acid, chebulinic acid, and gallic acid by HPLC method of analysis; and zinc by ICP-MS, and results are presented in Table-3. For comparative evaluation, 50% aqueous ethanol extract of *T. chebula* fruit without salt was also prepared (T.Ch). Similarly, *T. chebula* extract containing magnesium salt, calcium salt, and potassium salt are also prepared from 50% aqueous ethanol extract of *T. chebula* fruit, as described in examples 3-5.

*T. chebula* fruit extract enriched to chebulagic acid and chebulinic acid and their metal salts: Chebulagic acid and chebulinic acid are hydrolyzable tannoids, which are known to be responsible for several biological activities such as anti-oxidant, anti-inflammatory and anti-tumor etc. The extracts enriched in chebulagic acid and chebulinic acid were produced by eluting the *T. chebula* 50% aqueous ethanol extract solution through resin columns. Thus, 50% aqueous ethanol extract of *T. chebula* was loaded onto a PA-800 resin column and eluted with water, 10% ethanol/water, and finally with ethanol. Ethanol fraction was evaporated to get the enriched *T. chebula* extract, which was treated with zinc oxide to give the enriched extract containing zinc salt of chebulagic acid and/or zinc salt of chebulinic acid. Similarly, SP-700 and HP-20 resin columns also gave the *T. chebula* enriched extract containing metal salts (example 2).

Surprisingly, the inventors found that the *Terminalia chebula* extract containing metal salt of chebulagic acid, metal salt of chebulinic acid and metal salt of gallic acid; is more water-soluble than its corresponding extract without salt and the solubility data is presented in Table-4.

Salt formation: The chemical structures of chebulagic acid, chebulinic acid, and gallic acid contain a carboxylic acid group and phenolic hydroxyl groups that are capable of forming salt/complex with metal ions. *Terminalia chebula* extract containing these phytochemicals, when treated with metal oxides, metal hydroxides, metal carbonates, etc., forms metal salt or complex or chelate of chebulagic acid, chebulinic acid, and gallic acid. For example, treatment of *T. chebula* aqueous extract with zinc oxide gave *T. chebula* extract containing zinc salt or complex or chelate of chebulagic acid, chebulinic acid, and gallic acid. The presence of zinc by ICP-MS analysis of the extract (Table 3) clearly indicates the formation of salt. Further, *T. chebula* extract containing zinc salt is more water-soluble than the *T. chebula* extract without zinc salt (Table 4). Additionally, the acidity (pH) of *T. chebula* extract containing zinc salt is 5.5-5.9, whereas the extract without salt is 3.9, which also supports salt formation (Table 4).

To address the problem and to provide a safe herbal composition(s) for immune-boosting and respiratory health, the following cell-based assays have been chosen to evaluate the efficacy of the compositions in improving immunity and respiratory health.

(i) Interleukin-2 (IL-2) production (ii) Interferon-γ (IFN-γ) production

Interleukin-2: Interleukin-2 (IL-2) promotes T cell proliferation and differentiation in vitro and plays a crucial role during antigen-driven clonal expansion of T cells in vivo. For immune activation in vivo, IL-2 has a role in the proliferation and survival of T cells and differentiation of T cells into effector T cells. In chronic infection, IL-2 is also an important factor in generating memory T cells that undergo secondary expansion when they re-encounter the antigen. Alternatively, IL-2 can promote activation-induced cell death (AICD) of the T cells, down-regulating the immune response after the clonal expansion of antigen-specific T cells. IL-2 can also prime CD8+ T cells with non-infectious immunogens. Conversely, very high levels of IL-2 can bind to CD25 and differentiate the T cells into regulatory T cells (Tregs), which will suppress the excessive immune response. In this regard, compounds promoting IL-2 production are essential in boosting the host immune system.

Interferon-γ: Interferon-γ (IFN-γ) has been shown to have profound effects on both innate and adaptive immunity, which contribute to host protection. IFN-γ is produced by adaptive CD4+ Th1 T cells, CD8+ cytotoxic T cells, natural killer (NK) cells, B cells, NKT cells, and innate professional antigen-presenting cells (APCs) [monocyte/macrophage, dendritic cells (DC)]. IFN-γ has a critical role in recognizing and eliminating pathogens as it can coordinate a plethora of anti-microbial and anti-viral functions through cell-mediated immunity. It can enhance the antigen recognizing the capacity of APCs and amplify their antigen presentation to the T cells, subsequently increasing the production of reactive oxygen species (ROS) and reactive nitrogen intermediates (RNIs) and induce anti-viral responses. In the context of viral infections, INF-γ treatment can protect neurons from varicella-zoster virus and limit Hepatitis C virus proliferation in HIV patients. Importantly, IFN-γ plays a vital role in establishing a protective immune response to respiratory syncytial virus (RSV) infection. RSV is the leading cause of upper and lower respiratory tract infections, such as bronchiolitis and viral pneumonia. In this regard, compounds promoting INF-γ production would be potentially beneficial to boost the host immune system and improve respiratory health.

Hence, the *Terminalia chebula* extract containing zinc salt was evaluated for it's efficacy to improve IL-2 production and IFN-γ production in cellular models in comparison with *T. chebula* extract without zinc salt. Interestingly, the *T. chebula* extract containing zinc salt potently elevated the levels of said cytokines; and showed better improvement in the production of IL-2 and IFN-γ compared to the *T. chebula* extract without zinc salt.

For example, IL-2 production assay of *T. chebula* extract containing zinc salt (T.Ch.Zn-1) showed 20.67% increase in IL-2 production at 10 μg/mL, whereas *T. chebula* extract (without zinc salt) showed 7.11% increase in IL-2 production at 10 μg/mL. This is a surprising and unexpected result for enhancement of IL-2 production activity of the *T. chebula* extract containing zinc salt (T.Ch.Zn-1) compared to the corresponding *T. chebula* extract without zinc salt (Table-1).

TABLE 1

Percent increase in IL-2 and IFNγ production of the *Terminalia chebula* extract with zinc salt (T.Ch.Zn-1) and without salt (T.Ch)

| Extract | Product Description | % Increase in IL-2 production at 10 μg/mL | % Increase in IFN-γ production at 10 μg/mL |
|---|---|---|---|
| T.Ch | *T. chebula* extract (without zinc salt) | 7.11 | 8.19 |
| T.Ch.Zn-1 | *T. chebula* extract containing zinc salt | 20.67 | 18.36 |

Similarly, IFN-γ production assay of *T. chebula* extract containing zinc salt (T.Ch.Zn-1) showed 18.36% increase in IFN-γ levels at 10 μg/mL, whereas *T. chebula* extract (without salt) showed 8.19% increase in IFN-γ levels at 10 μg/mL. This is a surprising and unexpected result for enhancement of IFN-γ production activity of the *T. chebula* extract containing zinc salt compared to the corresponding *T. chebula* extract without salt (Table-1).

Thus the present invention provides *Terminalia chebula* extract containing metal salt of chebulagic acid, metal salt of chebulinic acid, and metal salt of gallic acid; wherein chebulagic acid can be in the range of 1.0-40%, chebulinic acid can be in the range of 1.0-30%, gallic acid can be in the range of 1.0-10% and metal can be present in the range of 0.5-5.0%; wherein the metal is selected from zinc, magnesium, calcium, and potassium.

Compositions

Encouraged by the improved efficacy of zinc salt of *Terminalia chebula* extract in increasing production of IL-2 and IFN-γ levels, the inventors have prepared compositions comprising *T. chebula* extract containing zinc salt in combination with at least one ingredient selected from extract, fraction, phytochemical or mixtures thereof derived from *Withania somnifera, Tinospora cordifolia* and *Andrographis paniculata*; to explore the efficacy of these compositions for improving immunity and respiratory health.

Thus, various solvent extracts of *Withania somnifera, Tinospora cordifolia*, or *Andrographis paniculata* were prepared with different solvents. For example, *W. somnifera* dried root was pulverized, and the powder was extracted with 60% aq ethanol, and the extract was concentrated to obtain 60% aq ethanol extract (W.S-1). Similarly, *W. somnifera* dried root powder was extracted with other solvents such as ethanol, water, 80% aqueous methanol and 80% aqueous acetone to obtain ethanol extract (W.S-2), water extract (W.S-3), 80% aqueous methanol extract (W.S-4), and 80% aqueous acetone extract (W.S-5) respectively. These extracts of *W. somnifera* root were standardized to total withanolides by analytical HPLC method of analysis, and the results are summarized in Table 5.

Similarly, *Tinospora cordifolia* dried stem raw material was pulverized, and the powder was extracted with water, 50% aq ethanol, and ethanol to obtain water extract (T.C-1), 50% aq ethanol extract (T.C-2), and ethanol extract (T.C-3), respectively. These extracts of *T. cordifolia* were standardized to 8-hydroxytinosporide by analytical HPLC method, and the results are summarized in Table 6. Similarly, *Andrographis paniculata* dried whole plant was pulverized, and the powder was extracted with 70% aq ethanol, water, and ethanol to obtain 70% aq ethanol extract (A.P-1), water extract (A.P-2), and ethanol extract (A.P-3), respectively. These extracts of *A. paniculata* were standardized to andrographolides by analytical HPLC method, and the results are summarized in Table 7.

The inventors then prepared two compositions, (a) composition-3 containing *Terminalia chebula* extract containing zinc salt (T.Ch.Zn-1) and *Withania somnifera* 60% aqueous ethanol extract (W.S-1) in the ratio of 1:1 and (b) composition-3A containing *Terminalia chebula* extract (T.Ch) and *Withania somnifera* 60% aqueous ethanol extract (W.S-1) in the ratio of 1:1, as a comparative composition without zinc salt. These two compositions were tested for their efficacy in increasing the production of IL-2 and IFN-γ in vitro cellular models, and the results are summarized in Table-2.

TABLE 2

Efficacy of composition comprising *Terminalia chebula* extract with zinc salt or regular extract without salt and *Withania somnifera* 60% aqueous ethanol extract

| Comp # | Composition Description | % Increase in IL-2 production at 10 μg/mL | % Increase in IFN-γ production at 10 μg/mL |
|---|---|---|---|
| Comp-3A | *T. chebula* extract without zinc salt (T.Ch) and *W. somnifera* 60% aqueous ethanol extract (W.S-1) in the ratio of 1:1 | 19.78 | 27.08 |
| Comp-3 | *T. chebula* extract containing zinc salt (T.Ch.Zn-1) and *W. somnifera* 60% aq ethanol extract (W.S-1) in the ratio of 1:1 | 39.78 | 41.08 |

From the above table, IL-2 production of the composition-3 comprising *T. chebula* extract containing zinc salt (T.Ch.Zn-1), and *W. somnifera* 60% aq ethanol extract (W.S-1) in the ratio of 1:1 increased by 39.78% at 10 μg/mL. While similar a composition without zinc salt (comp-3A) showed a 19.78% increase in IL-2 production at 10 μg/mL, this is a surprising and unexpected result for enhancement of IL-2 production activity of the composition-3 compared to the corresponding comparison example without zinc salt (Table-2). Similarly, composition-3 showed 41.08% increase in IFN-γ production at 10 μg/mL. While the similar composition without zinc salt (comp-3A) showed a 27.08% increase in IFN-γ production at 10 μg/mL. This is also a surprising and unexpected improvement. Hence, the compositions of *T. chebula* extract containing zinc salt with other herbal extracts such as *W. somnifera* showed better efficacy in increasing production of IL-2 and IFN-γ levels when compared to the compositions of *T. chebula* extract without zinc salt with other herbal extracts.

Following this surprise result, various compositions of *Terminalia chebula* extract containing metal salt of at least one phytochemical in the extract selected from chebulagic acid, chebulinic acid, and gallic acid or mixtures thereof; wherein the metal is selected from zinc, magnesium, calcium, and potassium; in combination with at least one extract derived from *Withania somnifera, Tinospora cordifolia* and *Andrographis paniculata* were prepared as summarized in examples 22-32.

Then, these compositions (C1-C35) were tested for their efficacy in increasing the production of IL-2, IFN-γ, and lymphocyte proliferation in vitro cellular models in comparison with the corresponding individual ingredients. Unexpectedly, these compositions showed synergistic activity.

For example, *Terminalia chebula* extract zinc salt (T.Ch.Zn-1) at 7.5 μg/mL concentration and *Withania somnifera* 60% aqueous ethanol extract (W.S-1) at 2.5 μg/mL concentration showed 15.50% and 5.83% increase in IL-2 production, respectively. The composition-1 (C-1) containing *T. chebula* extract zinc salt (T.Ch.Zn-1), and *W. somnifera* 60% aqueous ethanol extract (W.S-1) in the ratio of 3:1 at 10 μg/mL showed 31.04% increase in IL-2 production, which is significantly higher than the additive effect of 21.33% (15.50%+5.83%) calculated from the increase in IL-2 production showed by the corresponding individual ingredients. The compositions-2 to 5 (C-2 to C-5) containing these two extracts (T.Ch.Zn-1 and W.S-1) at ratios 2:1, 1:1, 1:2, and 1:3 respectively also exhibited synergism when compared to the increase in IL-2 production shown by each of their corresponding individual ingredient concentrations as summarized in Table 8. Similarly, the other compositions (C-6 to C-8) containing *T. chebula* enriched extract zinc salt (T.Ch.Zn-2) and *W. somnifera* 60% aqueous ethanol extract (W.S-1) also showed synergistic increase in IL-2 production as summarized in Table 8.

Similarly, the compositions (C-9 to C-14) comprising *T. chebula* extract containing zinc salt (T.Ch.Zn-1) and *Tinospora cordifolia* water extract (T.C-1) or *Andrographis paniculata* 70% aqueous ethanol extract (A.P-1); compositions (C-15 to C-23) comprising *T. chebula* extract containing magnesium salt (T.Ch.Mg) and *W. somnifera* ethanol extract (W.S-2) or *T. cordifolia* 50% aqueous ethanol extract (T.C-2) or *A. paniculata* water extract (A.P-2); compositions (C-24 to C-32) comprising *T. chebula* extract containing calcium salt (T.Ch.Ca) and *W. somnifera* 80% aqueous methanol extract (W.S-4) or *T. cordifolia* ethanol extract (T.C-3) or *A. paniculata* ethanol extract (A.P-3); compositions (C-33 to C-35) comprising *T. chebula* extract containing potassium salt (T.Ch.K) and *W. somnifera* 80% aqueous acetone extract (W. S-5) also showed synergistic improvements in IL-2 production (Tables 9-12).

Further, the compositions (1-35) also showed greater increase in INF-γ production than the corresponding individual ingredients. For example, *T. chebula* extract zinc salt (T.Ch.Zn-1) at 7.5 μg/mL concentration and *W. somnifera* 60% aqueous ethanol extract (W.S-1) at 2.5 μg/mL concentration showed 13.77% and 5.26% increase in INF-γ production, respectively. The composition-1 (C-1) containing these two extracts in the ratio of 3:1 at 10 μg/mL showed a 24.96% increase in INF-γ production, which is significantly higher than the additive effect of 19.03% (13.77%+5.26%) calculated from the increase in INF-γ production shown by the corresponding individual ingredients. The compositions-2 to 5 (C-2 to C-5) containing these two extracts at other ratios also exhibited synergism compared to the increase in INF-γ production shown by each of their corresponding individual ingredient concentrations as summarized in Table 13. Similarly, the other compositions (C-6 to C-8) containing zinc salt of *T. chebula* enriched extract (T.Ch.Zn-2) and *W. somnifera* 60% aqueous ethanol extract (W.S-1) also showed synergistic increase in INF-γ production (Table 13). Similarly, other compositions (C-9 to C-35) comprising *T. chebula* extract containing metal salts and one extract derived from *Withania somnifera, Tinospora cordifolia* extracts or *Andrographis paniculata*; also showed synergistic increase in INF-γ production (Tables 14-17). Further, these compositions (1-35) were also screened for their ability to increase lymphocyte proliferation and interestingly they all showed better increase of lymphocyte proliferation than the corresponding individual ingredients.

Lymphocyte Proliferation: The proliferation of lymphocytes, especially antigen-specific T cells, are critical for mediating protective immunity against bacterial/viral pathogens and to create immunological memory. Peripheral blood mononuclear cells (PBMCs) serve as an important cell population for proliferation assays. There are different methods to evaluate the cell proliferation, a. incorporation of 3H-thymidine into DNA of dividing cells, b. fluorescent dye dilution assays, using CFSE or its derivative, Oregon Green (OG), c. estimating Ki67 marker. Ki67 is a nuclear protein that plays a role in the regulation of cell division. It is expressed during all active phases of cell division but it is absent in quiescent cells and during DNA repair. Intracellular Ki67 expression directly in ex vivo, or after in vitro cell culture, has been used to measure specific T cell responses induced by vaccination or turnover of these cells in individuals with chronic viral infections, such as HIV infection. Ki67 evaluation is an important tool to evaluate the efficacy of compounds that promote PBMC proliferation in general and T cells in particular.

Lymphocytes are the major cellular components of the immune system and are responsible for developing adaptive immune responses in the host. Increased lymphocyte population through an enhanced proliferation of the precursor hematopoietic cells is essential to build a strong cell-mediated immune response in the body against bacterial or viral infections.

For example, zinc salt of *T. chebula* extract (T.Ch.Zn-1) at 7.5 μg/mL concentration, and *W. somnifera* 60% aqueous ethanol extract (W.S-1) at 2.5 μg/mL concentration showed 10.04% and 4.21% increase in lymphocyte proliferation, respectively. The composition-1 (C-1) containing these two extracts in the ratio of 3:1 at 10 μg/mL showed a 20.03% increase of lymphocyte proliferation, which is significantly better than the additive effect of 14.25% (10.04%+4.21%) calculated from the increase in lymphocyte proliferation showed by the corresponding individual ingredients. The compositions 2-5 (C-2 to C-5) containing these two extracts at other ratios also exhibited synergism when compared to the increase of lymphocyte proliferation shown by each of their corresponding individual ingredient concentrations, as summarized in Table 18. Similarly, the other compositions (C-6 to C-8) containing zinc salt of *T. chebula* enriched extract (T.Ch.Zn-2) and *W. somnifera* 60% aqueous ethanol extract (W.S-1) also showed synergistic increase in lymphocyte proliferation (Table 18). Similarly, compositions (C-9 to C-35) comprising *T. chebula* extract containing metal salts and one extract derived from *Withania somnifera, Tinospora cordifolia* extracts or *Andrographis paniculata*; also showed synergistic increase in lymphocyte proliferation (Tables 19-21).

Modulation of inflammation and immune response in rats: These compositions comprising *Terminalia chebula* extract containing metal salt of at least one phytochemical selected from chebulagic acid, chebulinic acid, and gallic acid or mixtures thereof; and one additional extract selected from *Withania somnifera, Tinospora cordifolia*, and *Andrographis paniculata*; were evaluated for modulation of inflammation and immune response in rats.

Cluster of differentiation 3 (CD3) is a multimeric protein complex, a unique co-receptor to the T-cell lineage. It is expressed in the early stage of T cell maturation. CD3 positive cells (CD3+) are involved in activating the CD4+ naïve T cells (helper T cells) and CD8+ naïve T cells (cytotoxic T cells). After being triggered, CD4+ T cells differentiate into the functional subsets—T helper type 1 (TH1) and T helper type 2 (TH2) cells. The TH1 and TH2 cells produce cytokines IFN-γ and IL-4, respectively. The T helper cells are essential for eliciting immune protection against various intracellular and extracellular infections caused by viruses and bacteria. CD8+ T cells mediate their effector functions by producing cytokines such as IFN-γ and TNF-α and/or by cytolytic processes. Together, the different subsets of T-lymphocytes are integral parts of the host cellular immune system that are important in preventing or maintaining the immune defense against infection or disease.

Immunoglobulin G (IgG) is a class of antibodies that constitutes approximately two-thirds of the total antibodies present in the body. Immunoglobulins are essential for producing the humoral immune response and critical for the host's defense against infection. IgGs are produced by the plasma-B cells when stimulated by an antigenic response from an infection. Essentially, the IgGs contribute to neutralizing pathogens in the phagocytic cells.

In the above context, a compound that increases populations of the T-cell subsets (CD3+, CD4+, and CD8+) and elevates the IgG level in the body would be potentially valuable to boost the host immune defense through eliciting the cellular and humoral immunity against infection.

IL-6 is a pro-inflammatory cytokine produced by the cells from the innate immune system (e.g., macrophages, dendritic cells, mast cells, neutrophils). The levels of IL-6 in serum are elevated in many inflammatory conditions. Hence, IL-6 is considered a general marker of inflammation. Different stimuli, including allergens, respiratory viruses, elicit an inflammatory response in the lung epithelial cells and elevates serum IL-6 level. Therefore, a compound that reduces the IL-6 level in serum would be beneficial to alleviate the systemic inflammation that includes inflammation in the lungs due to exposure to allergens or microbial pathogens.

Thus the biomarkers that modulate inflammation and immune response were explored in vivo in experimental rats. The present observations reveal that the rats supplemented with the inventive compositions showed synergistic improvements in the modulation of the biomarkers such as $CD3^+$ population, $CD4^+$+ $CD8^+$ population, IL-6, and IgG when compared to the LPS-induced rats (Tables 22-24).

Increase of $CD3^+$ and $CD4^+$+ $CD8^+$ population: The present compositions showed synergistic efficacy in increasing $CD3^+$ and $CD4^+$+ $CD8^+$ population in the experimental animals. For example, *Withania somnifera* 60% aqueous ethanol extract (W.S-1) and *Terminalia chebula* extract containing zinc (T.Ch.Zn-1) showed 7.79% and 7.17% increase respectively in the $CD3^+$ population, compared to that found in LPS-induced rats with the supplementation. The composition-36 containing these two extracts at 1:1 ratio along with excipients showed a 16.51% increase in $CD3^+$ population from the LPS-induced rats (Table 22), which is a significantly higher increase than the efficacy shown by the corresponding individual ingredients, suggesting an in vivo synergistic effect between *W. somnifera* 60% aqueous ethanol extract (W.S-1) and *T. chebula* extract containing zinc (T.Ch.Zn-1) in increasing $CD3^+$ population. Similarly, *W. somnifera* 60% aqueous ethanol extract (W.S-1) and *T. chebula* extract containing zinc (T.Ch.Zn-1) showed 8.05% and 7.28% increase in the $CD4^+$+ $CD8^+$ population, respectively when compared to the LPS induction group (G2) rats (Table 23). The composition-36 containing these two extracts at a 1:1 ratio along with excipients showed 18.39% increase from the LPS-induced group (G2), which is a significantly higher increase than the corresponding individual ingredients, suggesting a synergistic effect between these two extracts in increasing $CD4^+$+ $CD8^+$ population.

Reduction of IL-6 and increase in IgG levels: The present compositions also showed synergistic efficacy in reducing IL-6 and increasing IgG levels in the experimental animals. For example, *W. somnifera* 60% aqueous ethanol extract (W.S-1) and *T. chebula* extract containing zinc (T.Ch.Zn-1) showed 18.3% and 15.5% reduction in IL-6 levels, respectively when compared to the IL-6 levels found in LPS-induced rats. The composition-36 containing these two extracts at a 1:1 ratio along with excipients showed 29.4% reduction compared to the LPS-induced rats, which is a significantly greater reduction than the corresponding individual ingredients, suggesting a synergistic effect between these two extracts in decreasing serum IL-6. Similarly, composition-36 showed a significantly higher increase in IgG level than the corresponding individual ingredients, suggesting a synergistic effect between W.S-1 and T.Ch.Zn-1 in increasing IgG as summarized in Table-24.

Hence, these compositions (C1 to C35) unexpectedly showed better efficacy in increasing the production of IL-2, IFN-γ, and lymphocyte proliferation when compared to their corresponding individual ingredients. Thus, the compositions comprising a first ingredient *Terminalia chebula* extract containing metal salt of at least one phytochemical in the extract selected from chebulagic acid, chebulinic acid, and gallic acid or mixtures thereof; and a second ingredient selected from extract(s), fraction(s), phytochemical(s) or mixtures thereof derived from *Withania somnifera, Tinospora cordifolia* and *Andrographis paniculata*; have the tendency to show synergism when combined together.

Process: The process for the preparation of synergistic compositions comprising a first ingredient *Terminalia chebula* extract containing metal salt of at least one phytochemical in the extract selected from chebulagic acid, chebulinic acid, and gallic acid or mixtures thereof; and a second ingredient selected from at least one extract(s), fraction(s), phytochemical(s) or mixtures thereof derived from *Withania somnifera, Tinospora cordifolia*, and *Andrographis paniculata*; wherein the process comprises the following steps of;

(i) extracting dried *Terminalia chebula* fruit powder with suitable solvent;
(ii) optionally, the extract from step (i) eluted through resin column to get enriched extract;
(iii) treating the solution in step ii with a metal compound;
(iv) filtering the solution;
(v) evaporating the solvent and drying the residue to obtain the *Terminalia chebula* extract containing metal salt;

(vi) blending the *Terminalia chebula* extract containing metal salt with at least one extract derived from *Withania somnifera* or *Tinospora cordifolia* or *Andrographis paniculata* in the presence of pharmaceutically or nutraceutically or dietically acceptable excipients, carriers, and diluents;

(vii) drying the product under vacuum to get the composition.

The suitable solvent used in the process for the preparation of compositions is selected from but not limited to; C1-C5 alcohols, like ethanol, methanol, n-butanol; water, and mixtures thereof. The metal used in the process for the preparation of the compositions is selected from zinc, magnesium, calcium, and potassium, and the metal compound used for the preparation of these compositions is in the form of their metal salts, metal oxides, metal hydroxides, or carbonates. Examples include zinc oxide, zinc carbonate, zinc hydroxide, magnesium oxide, magnesium carbonate, magnesium hydroxide, calcium hydroxide, calcium carbonate, potassium hydroxide, potassium carbonate. The resin column used in the process for the preparation of the compositions is selected from PA-800, SP-700, and HP-20.

Formulations: The present invention also provides synergistic herbal compositions comprising a first ingredient *Terminalia chebula* extract containing metal salt of at least one phytochemical in the extract selected from chebulagic acid, chebulinic acid, and gallic acid or mixtures thereof; and a second ingredient selected from extract(s), fraction(s), phytochemical(s) or mixtures thereof derived from *Withania somnifera, Tinospora cordifolia* and *Andrographis paniculata*; the composition may be formulated with at least one component selected from pharmaceutically or nutraceutically or dietically acceptable excipients, carriers and diluents.

The synergistic herbal compositions comprising a first ingredient *Terminalia chebula* extract containing metal salt; and a second ingredient selected from extract(s), fraction(s), phytochemical(s) or mixtures thereof derived from *Withania somnifera, Tinospora cordifolia* and *Andrographis paniculata*; and containing at least one component selected from pharmaceutically or nutraceutically or dietically acceptable excipients, carriers and diluents; for obtaining at least one health benefit selected from improve immunity/elicit immune response/rejuvenating the immune system, improve innate immunity, improve adaptive immunity, improve cellular immunity, improve humoral immunity, strengthen natural defense, improving protection from airway inflammation and microbial infection, preventing viral respiratory infections and improvement of respiratory/lungs health; wherein the pharmaceutically or nutraceutically or dietically acceptable excipients, carriers and diluents are selected from monosaccharide's such as glucose, dextrose, fructose, galactose etc.; disaccharides such as but not limited to sucrose, maltose, lactose, lactulose, trehalose cellobiose, chitobiose etc.; polycarbohydrates such as starch and modified starch such as sodium starch glycolate, pre-gelatinized starch, soluble starch, and other modified starches; dextrins that are produced by hydrolysis of starch or glycogen such as yellow dextrin, white dextrin, maltodextrin etc.; polyhydric alcohols or sugar alcohols such as but not limited to sorbitol, mannitol, inositol, xylitol, isomalt etc.; cellulose based derivatives such as but not limited to microcrystalline cellulose, hydroxy propyl methyl cellulose, hydroxy ethyl cellulose etc.; silicates such as but not limited to neusilin, veegum, talc, colloidal silicon dioxide etc.; metallic stearates such as but not limited to calcium stearate, magnesium stearate, zinc stearate etc.; organic acids such as citric acid, tartaric acid, malic acid, succinic acid, lactic acid, L-ascorbic acid etc.; fatty acid esters and esters of poly sorbate, natural gums such as but not limited to acacia, carrageenan, guar gum, xanthan gum etc.; vitamin B group, nicotinamide, calcium pantothenate, amino acids, proteins such as but not limited to casein, gelatin, pectin, agar; organic metal salts such as but not limited to sodium chloride, calcium chloride, dicalcium phosphate, zinc sulphate, zinc chloride etc.; natural pigments, flavors, class I & class II preservatives and aqueous, alcoholic, hydro-alcoholic, organic solutions of above listed ingredients alone or in combination.

The foregoing demonstrates that synergistic herbal compositions comprising a first ingredient *Terminalia chebula* extract containing metal salt or metal complex or metal chelate of at least one phytochemical in the extract selected from chebulagic acid, chebulinic acid, and gallic acid or mixtures thereof; wherein the metal is selected from zinc, magnesium, calcium and potassium; and a second ingredient selected from extract(s), fraction(s), phytochemical(s) or mixtures thereof derived from *Withania somnifera, Tinospora cordifolia* and *Andrographis paniculata*; unexpectedly showed better efficacy in increasing the production of IL-2, IFN-γ and lymphocyte proliferation when compared to their corresponding individual ingredients. Hence, the said compositions can be useful for ameliorating immunity, lung function and respiratory health.

Therefore, in an important embodiment, the present invention provides synergistic compositions comprising a first ingredient *Terminalia chebula* extract containing metal salt or metal complex or metal chelate of at least one phytochemical in the extract selected from chebulagic acid, chebulinic acid, and gallic acid or mixtures thereof; wherein the metal is selected from zinc, magnesium, calcium and potassium; and a second ingredient selected from extract(s), fraction(s), phytochemical(s) or mixtures thereof derived from *Withania somnifera, Tinospora cordifolia* and *Andrographis paniculata*; for obtaining at least one health benefit selected from improving immunity/eliciting immune response/rejuvenating the immune system, improving innate immunity, improving adaptive immunity, improving cellular immunity, improving humoral immunity, strengthening the natural defense, improving protection from airway inflammation and microbial infection, preventing viral respiratory infections and improving lung function/health and improving respiratory health.

In one preferred embodiment, the present invention provides synergistic compositions comprising a first ingredient *Terminalia chebula* extract containing zinc salt of at least one phytochemical in the extract selected from chebulagic acid, chebulinic acid, and gallic acid or mixtures thereof; and a second ingredient selected from extract(s), fraction(s), phytochemical(s) or mixtures thereof derived from *Withania somnifera, Tinospora cordifolia* and *Andrographis paniculata*; for ameliorating immunity and respiratory/lungs health.

In one preferred embodiment, the present invention provides synergistic compositions comprising a first ingredient *Terminalia chebula* extract containing magnesium salt of at least one phytochemical in the extract selected from chebulagic acid, chebulinic acid, and gallic acid or mixtures thereof; and a second ingredient selected from extract(s), fraction(s), phytochemical(s) or mixtures thereof derived from *Withania somnifera, Tinospora cordifolia* and *Andrographis paniculata*; for ameliorating immunity and respiratory/lungs health.

In one preferred embodiment, the present invention provides synergistic compositions comprising a first ingredient

*Terminalia chebula* extract containing calcium salt of at least one phytochemical in the extract selected from chebulagic acid, chebulinic acid, and gallic acid or mixtures thereof; and a second ingredient selected from extract(s), fraction(s), phytochemical(s) or mixtures thereof derived from *Withania somnifera, Tinospora cordifolia* and *Andrographis paniculata*; for ameliorating immunity and respiratory/lungs health.

In one preferred embodiment, the present invention provides synergistic compositions comprising a first ingredient *Terminalia chebula* extract containing potassium salt of at least one phytochemical in the extract selected from chebulagic acid, chebulinic acid, and gallic acid or mixtures thereof; and a second ingredient selected from extract(s), fraction(s), phytochemical(s) or mixtures thereof derived from *Withania somnifera, Tinospora cordifolia* and *Andrographis paniculata*; for ameliorating immunity and respiratory/lungs health.

In another embodiment, the present invention provides synergistic compositions comprising a first ingredient *Terminalia chebula* extract containing metal salt of at least one phytochemical in the extract selected from chebulagic acid, chebulinic acid, and gallic acid or mixtures thereof; and a second ingredient selected from extract(s), fraction(s), phytochemical(s) or mixtures thereof derived from *Withania somnifera, Tinospora cordifolia* and *Andrographis paniculata*; wherein chebulagic acid is in the range of 1.0-40%, chebulinic acid is in the range of 1.0-30%, gallic acid is in the range of 1.0-10%, and metal is in the range of 0.5-5.0%; wherein the metal is selected from zinc, magnesium, calcium, and potassium.

In another embodiment, the present invention provides synergistic compositions comprising a first ingredient *Terminalia chebula* extract containing metal salt of at least one phytochemical in the extract selected from chebulagic acid, chebulinic acid, and gallic acid or mixtures thereof and a second ingredient selected from extract(s), fraction(s), phytochemical(s) or mixtures thereof derived from *Withania somnifera, Tinospora cordifolia* and *Andrographis paniculata*; wherein the concentration of *Terminalia chebula* extract containing metal salt in the composition varies in the range of 10%-90% by weight and the concentration of second extract, fraction or phytochemical derived from *Withania somnifera or Tinospora cordifolia* or *Andrographis paniculata*; in the composition varies in the range of 90%-10% by weight.

In another embodiment, the present invention provides synergistic compositions comprising a first ingredient *Terminalia chebula* extract containing metal salt of at least one phytochemical in the extract selected from chebulagic acid, chebulinic acid, and gallic acid or mixtures thereof and a second ingredient selected from extract(s), fraction(s), phytochemical(s) or mixtures thereof derived from *Withania somnifera, Tinospora cordifolia* and *Andrographis paniculata*; wherein the extract or fraction is obtained from at least one plant part selected from the group comprising leaves, stems, tender stems, tender twigs, aerial parts, whole fruit, fruit peel rind, seeds, flower heads, root, bark, hardwood, rhizome or whole plant or mixtures thereof.

In another embodiment, the present invention provides synergistic herbal compositions as disclosed above; wherein the extract, fraction, phytochemical or mixtures thereof; are produced using at least one solvent selected from C1-C5 alcohols selected from ethanol, methanol, n-propanol, isopropyl alcohol; ketones selected from acetone, methyl-isobutyl ketone; chlorinated solvents selected from methylene dichloride and chloroform; water and mixtures thereof C1-C7 hydrocarbons such as hexane; esters like ethyl acetate and the like and mixtures thereof.

In another embodiment, the present invention provides synergistic herbal compositions as described above; wherein the extract, fraction, or mixtures thereof; in the composition are standardized to at least one phytochemical reference marker compound or pharmacologically active marker; wherein phytochemical marker compound or group of phytochemical compounds is in the concentration range of 0.01% to 90% by weight of the extract.

In another embodiment, the present invention provides synergistic herbal compositions as described above, wherein said *Withania somnifera* root extract or fraction is standardized to total withanolides; wherein total withanolides are in the concentration range of 0.01% to 10% by weight of the composition.

In another embodiment, the present invention provides synergistic herbal compositions as described above, wherein said *Tinospora cordifolia* stem extract or fraction is standardized to 8-hydroxytinosporide; wherein 8-hydroxytinosporide is in the concentration range of 0.01% to 5% by weight of the composition.

In another embodiment, the present invention provides synergistic herbal compositions as described above; wherein said *Andrographis paniculata* whole plant extract or fraction is standardized to andrographolides; wherein total andrographolides are in the concentration range of 1.00% to 40% by weight of the composition.

In another embodiment, the present invention provides synergistic compositions comprising a first ingredient *Terminalia chebula* extract containing metal salt of at least one phytochemical in the extract selected from chebulagic acid, chebulinic acid, and gallic acid or mixtures thereof; and a second ingredient selected from extract(s), fraction(s), phytochemical(s) or mixtures thereof derived from *Withania somnifera, Tinospora cordifolia* and *Andrographis paniculata*; further containing optionally at least one component selected from pharmaceutically or nutraceutically or dietically acceptable excipients, carriers and diluents.

In another embodiment, the present invention provides synergistic compositions comprising a first ingredient *Terminalia chebula* extract containing metal salt of at least one phytochemical in the extract selected from chebulagic acid, chebulinic acid, and gallic acid or mixtures thereof; and a second ingredient selected from extract(s), fraction(s), phytochemical(s) or mixtures thereof derived from *Withania somnifera, Tinospora cordifolia* and *Andrographis paniculata*; further containing optionally at least one component selected from pharmaceutically or nutraceutically or dietically acceptable excipients, carriers and diluents; wherein the pharmaceutically or nutraceutically or dietically acceptable excipients, carriers and diluents are selected from monosaccharide's such as glucose, dextrose, fructose, galactose etc.; disaccharides such as but not limited to sucrose, maltose, lactose, lactulose, trehalose cellobiose, chitobiose etc.; polycarbohydrates such as starch and modified starch such as sodium starch glycolate, pre-gelatinized starch, soluble starch, and other modified starches; dextrins that are produced by hydrolysis of starch or glycogen such as yellow dextrin, white dextrin, maltodextrin etc.; polyhydric alcohols or sugar alcohols such as but not limited to sorbitol, mannitol, inositol, xylitol, isomalt etc.; cellulose based derivatives such as but not limited to microcrystalline cellulose, hydroxy propyl methyl cellulose, hydroxy ethyl cellulose etc.; silicates such as but not limited to neusilin, veegum, talc, colloidal silicon dioxide etc.; metallic stearates such as but not limited to calcium stearate, magnesium stearate, zinc stearate etc.; organic acids such as citric acid, tartaric acid, malic acid, succinic acid, lactic acid, L-ascorbic acid etc.; fatty acid esters and esters of poly sorbate, natural gums such as but not limited to acacia, carrageenan, guar gum, xanthan gum etc.; vitamin B group, nicotinamide, calcium pantothenate, amino acids, proteins such as but not limited to casein, gelatin, pectin, agar; organic metal salts such as but not limited to sodium chloride, calcium chloride, dicalcium phosphate, zinc sulphate, zinc chloride etc.; natural pigments, flavors, class I & class II preservatives and aqueous, alcoholic, hydro-alcoholic, organic solutions of above listed ingredients alone or in combination.

In another embodiment, the present invention provides a process for the preparation of synergistic compositions comprising a first ingredient *Terminalia chebula* extract containing metal salt of at least one phytochemical in the extract selected from chebulagic acid, chebulinic acid, and gallic acid or mixtures thereof and second ingredient selected from extract(s), fraction(s), phytochemical(s) or mixtures thereof derived from *Withania somnifera, Tinospora cordifolia*, and *Andrographis paniculata*; wherein the process comprises the following steps of;

(i) extracting dried *Terminalia chebula* fruit powder with suitable solvent;
(ii) optionally, the extract from step (i) is eluted through resin column to get enriched extract;
(iii) treating the extract solution obtained from steps i or ii with a metal compound;
(iv) filtering the solution;
(v) evaporating the solvent and drying the residue to obtain the *Terminalia chebula* extract containing metal salt;
(vi) blending the *Terminalia chebula* extract containing metal salt with at least one extract derived from *Withania somnifera* or *Tinospora cordifolia* or *Andrographis paniculata* in the presence of at least one component selected from pharmaceutically or nutraceutically or dietically acceptable excipients, carriers, and diluents;
(vii) drying the product under vacuum to get the composition.

In another embodiment, the present invention provides a process for the preparation of compositions as described above, wherein the suitable solvent used in the process for the preparation of compositions is selected from but not limited to; C1-C5 alcohols, like ethanol, methanol, n-butanol; water and mixtures thereof.

In another embodiment, the present invention provides process for the preparation of compositions as described above; wherein the metal is selected from zinc, magnesium, calcium and potassium; and the metal compound used for the preparation of these compositions is in the form of their metal salts, metal oxides, metal hydroxides or carbonates. Examples include zinc oxide, zinc carbonate, zinc hydroxide, magnesium oxide, magnesium carbonate, magnesium hydroxide, calcium hydroxide, calcium carbonate, potassium hydroxide, potassium carbonate.

In another embodiment, the present invention provides a process for the preparation of compositions as described above, wherein resin column is selected from PA-800, SP-700, and HP-20.

In another embodiment, the present invention provides method of obtaining at least one health benefit selected from improving immunity/eliciting immune response/rejuvenating the immune system, improving innate immunity, improving adaptive immunity, improving cellular immunity, improving humoral immunity, strengthen natural defense, improving protection from airway inflammation and microbial infection, preventing viral respiratory infections, improving lung function/health and improving respiratory health in a human; wherein the method comprises supplementing human with an effective dose of a composition comprising a first ingredient *Terminalia chebula* extract containing metal salt or metal complex or metal chelate of at least one phytochemical in the extract selected from chebulagic acid, chebulinic acid and gallic acid or mixtures thereof and a second ingredient selected from extract(s), fraction(s), phytochemical(s) or mixtures thereof derived from *Withania somnifera, Tinospora cordifolia* and *Andrographis paniculata*; optionally containing at least one component selected from pharmaceutically or nutraceutically or dietically acceptable excipients, carriers and diluents.

In another embodiment, the present invention provides the use of a synergistic composition comprising a first ingredient *Terminalia chebula* extract containing metal salt or metal complex or metal chelate of at least one phytochemical in the extract selected from chebulagic acid, chebulinic acid and gallic acid or mixtures thereof and a second ingredient selected from extract(s), fraction(s), phytochemical(s) or mixtures thereof derived from *Withania somnifera, Tinospora cordifolia* and *Andrographis paniculata*; optionally containing at least one component selected from pharmaceutically or nutraceutically or dietically acceptable excipients, carriers and diluents; for obtaining at least one health benefit selected from improving immunity/elicit immune response/rejuvenating the immune system, improving innate immunity, improving adaptive immunity, improving cellular immunity, improving humoral immunity, strengthen the natural defense, improving protection from airway inflammation and microbial infection, preventing viral respiratory infections and improving lung function/health and improving respiratory health.

In another embodiment of the invention, the composition as disclosed above is formulated into a dosage form selected from dry powder form, liquid form, beverage, food product, dietary supplement, or any suitable form such as a tablet, a capsule, a soft chewable or gummy bear.

In another embodiment of the invention, the compositions as disclosed above can be formulated into nutritional/dietary supplements that can be contemplated/made into the dosage form of healthy foods, or food for specified health uses such as solid food like chocolate or nutritional bars, semisolid food like cream, jam, or gel or beverage such as refreshing beverage, lactic acid bacteria beverage, drop, candy, chewing gum, gummy candy, yogurt, ice cream, pudding, soft adzuki bean jelly, jelly, cookie, tea, soft drink, juice, milk, coffee, cereal, snack bar and the like.

Those of ordinary skilled in the art will appreciate that changes could be made to the embodiments described above without departing from the broad inventive concept thereof. It is understood, therefore, that this invention is not limited to the particular embodiments or examples disclosed herein, but is intended to cover modifications within the objectives and scope of the present invention as defined in the specification. The examples are given solely for the purpose of illustration and are not to be construed as limitations of the present disclosure, as many variations thereof possible without departing from the spirit of the disclosure.

EXAMPLES

Example 1: *Terminalia Chebula* Extract Containing Zinc Salt of Chebulagic Acid and/or Zinc Salt of Chebulinic Acid and/or Zinc Salt of Gallic Acid (T.Ch.Zn-1)

To the dried whole fruit powder of *Terminalia chebula* (500 g) was added 50% aqueous ethanol (5 L), and the mixture was extracted at ambient temperature for 16 h. The mixture was filtered through celite, and the extraction process was repeated with 50% aqueous ethanol (2×3 L) under similar conditions for 2 h. To the combined 50% aqueous ethanol extract was added zinc oxide (8.1 g), and the mixture was stirred at ambient temperature for 2 h. The mixture was filtered, and the filtrate was evaporated under vacuum to give the product as a brown color solid (T.Ch.Zn-1, 178 g).

Example 1A: *Terminalia Chebula* Extract (T.Ch)

For comparison, *Terminalia chebula* extract (T.Ch) without the salt is prepared using the following procedure. To the dried whole fruit powder of *Terminalia chebula* (50 g) was added 50% aqueous ethanol (500 mL), and the mixture was extracted at ambient temperature for 16 h. The mixture was filtered through celite and the extraction process was repeated with 50% aqueous ethanol (2×300 mL) under similar conditions for 2 h. The combined 50% aqueous ethanol extract was evaporated under reduced pressure to give the product as a brown color solid (T.Ch, 23 g).

Example 2: *Terminalia Chebula* Enriched Extract Containing Zinc Salt of Chebulagic Acid and/or Zinc Salt of Chebulinic Acid and/or Zinc Salt of Gallic Acid Method 1 (T.Ch.Zn-2): To the dried whole fruit powder of *Terminalia chebula* (50 g) was added 50% aqueous ethanol (500 mL) and the mixture was extracted at ambient temperature for 16 h. The mixture was filtered through celite, and the extraction process was repeated on the left over residue with 50% aqueous ethanol (2×300 mL) under similar conditions for 2 h. The combined 50% aqueous ethanol extract was evaporated under reduced pressure to give a concentrated extract. To the concentrated extract was added water (1000 mL), and the solution was loaded onto 230 mL of PA-800 resin with a flow rate of 20 mL per minute. After loading the extract, the column was eluted sequentially with water (230 mL), 10% ethanol/water (230 mL), and finally with ethanol (350 mL). The fractions eluted with ethanol were collected separately and were combined. The combined ethanol fraction was evaporated under reduced pressure to give a concentrated extract and it was then diluted with water (200 mL). To this mixture was added zinc oxide (808 mg) and was stirred at ambient temperature for 2 h. The mixture was filtered, and the filtrate was evaporated under reduced pressure to give the product as a brown color solid (T.Ch.Zn-2, 7.35 g).

Method 2: *Terminalia chebula* extract containing zinc salt was prepared from *Terminalia chebula* (50 g) as described in method-1 by replacing PA-800 resin with SP-700 resin to give the product as a brown color solid (8.0 g).

Method 3: *Terminalia chebula* extract containing zinc salt was prepared from *Terminalia chebula* (50 g) as described in method-1 by replacing PA-800 resin with HP-20 resin to give the product as a brown color solid (6.8 g).

Example 3: *Terminalia Chebula* Extract Containing Magnesium Salt of Chebulagic Acid and/or Magnesium Salt of Chebulinic Acid and/or Magnesium Salt of Gallic Acid (T.Ch.Mg)

*Terminalia chebula* extract containing magnesium salt was prepared from *Terminalia chebula* (50 g) as described in example-1 or 2 by replacing zinc oxide with magnesium oxide (667 mg) to give the product as a brown color solid (T.Ch.Mg, 18.3 g).

Example 4: *Terminalia Chebula* Extract Containing Calcium Salt of Chebulagic Acid and/or Calcium Salt of Chebulinic Acid and/or Calcium Salt of Gallic Acid (T.Ch.Ca)

*Terminalia chebula* extract containing calcium salt was prepared from *Terminalia chebula* (50 g) as described in example-1 or 2 by replacing zinc oxide with calcium oxide (556 mg) to give the product as a brown color solid (T.Ch.Ca, 18.7 g).

Example 5: *Terminalia Chebula* Extract Containing Potassium Salt of Chebulagic Acid and/or Potassium Salt of Chebulinic Acid and/or Potassium Salt of Gallic Acid (T.Ch.K)

*Terminalia chebula* extract containing potassium salt was prepared from *Terminalia chebula* (50 g) as described in example-1 or 2 by replacing zinc oxide with potassium carbonate (1.13 g) to give the product as a brown color solid (T.Ch.K, 18.0 g).

Alternatively, *Terminalia chebula* extract containing metal salt of chebulagic acid and/or chebulinic acid and/or gallic acid were also prepared from *Terminalia chebula* whole fruit water extract with zinc oxide or magnesium oxide or calcium oxide or potassium carbonate.

Example 6: Standardization of *Terminalia Chebula* Extracts Containing Metal Salts

*Terminalia chebula* extracts containing metal salts disclosed above were analyzed for chebulagic acid, chebulinic acid, and gallic acid by analytical HPLC. The concentrations of metals such as zinc, magnesium, calcium, and potassium were analyzed by ICP-MS, and the results are summarized in Table 3.

TABLE 3

Analysis data of *T. chebula* extracts containing metal salts

| Example # | Chebulagic acid (1) | Chebulinic acid (2) | Gallic acid (3) | Sum of 1 + 2 + 3 | Metal |
|---|---|---|---|---|---|
| 1A | 10.05% | 4.90% | 2.6% | 17.55% | — |
| 1 | 10.26% | 4.80% | 2.81% | 17.87% | Zn: 1.0% |
| 2 (method 1) | 20.03% | 10.41% | 0.87% | 31.31% | Zn: 2.79% |
| 2 (method 2) | 18.56% | 8.98% | 0.72% | 28.26% | Zn: 2.45% |
| 2 (method 3) | 22.26% | 12.35% | 0.89% | 35.50% | Zn: 2.86% |
| 3 | 10.33% | 5.44% | 3.10% | 18.87% | Mg: 1.2% |
| 4 | 11.14% | 5.73% | 2.97% | 19.84% | Ca: 1.3% |
| 5 | 8.79% | 4.12% | 3.11% | 16.02% | K: 1.8% |

Example 7: Solubility and pH Data of *Terminalia Chebula* Extracts Containing Metal Salts

*Terminalia chebula* extracts containing metal salts disclosed above were evaluated for their solubility in water through a stepwise procedure by increasing the volume of water and also determined their pH. The results are summarized in Table-4.

TABLE 4

Solubility and pH data of *T. chebula* extracts containing metal salts

| Example # | Extract code | Solubility of 1.0 g of product in water | pH (1% solution) |
|---|---|---|---|
| 1A (regular extract) | T.Ch | >1000 mL | 3.9 |
| 1 | T.Ch.Zn-1 | 10 mL | 5.5 |
| 2 (method 1) | T.Ch.Zn-2 | 20 mL | 5.6 |
| 3 | T.Ch.Mg | 10 mL | 5.9 |
| 4 | T.Ch.Ca | 10 mL | 5.5 |
| 5 | T.Ch.K | 10 mL | 5.8 |

Example 8: *Withania Somnifera* 60% Aqueous Ethanol Extract (W.S-1)

To dried root powder of *Withania somnifera* (50 Kg) was added 60% aqueous ethanol (300 L), and the mixture was extracted at ambient temperature for 16 h. The mixture was filtered, and the extraction process was repeated with 60% aqueous ethanol (2×200 L) under similar conditions for 2 h. The combined 60% aqueous ethanol extract was evaporated under reduced pressure to give the product as a brown color solid (W.S-1, 8.9 Kg).

Example 9: *Withania Somnifera* Ethanol Extract (W.S-2)

The ethanol extract (W.S-2, 2.55 g) was obtained from 100 g raw material by adopting a similar procedure using ethanol as an extraction solvent.

Example 10: *Withania Somnifera* Water Extract (W.S-3)

The water extract (W.S-3; 15.8 g) was obtained from 100 g raw material by adopting a similar procedure using water as an extraction solvent.

Example 11: *Withania Somnifera* 80% Aqueous Methanol Extract (W.S-4)

The 80% aqueous methanol extract (W.S-4; 14.5 g) was obtained from 100 g raw material by adopting a similar procedure using 80% aqueous methanol as an extraction solvent.

Example 12: *Withania Somnifera* 80% Aqueous Acetone Extract (W.S-5)

The 80% aqueous acetone extract (W.S-5; 9.5 g) was obtained from 100 g raw material by adopting a similar procedure using 80% aqueous acetone as an extraction solvent.

Example 13: Standardization of *Withania Somnifera* Extracts

The various extracts of *Withania somnifera* were standardized to total withanolides by the analytical HPLC method (USP method), and the results are summarized in Table 5.

TABLE 5

Details of *Withania somnifera* extracts

| Example # | Extract code | Solvent used for extraction | Total withanolides by HPLC |
|---|---|---|---|
| 8 | W.S-1 | 60% aqueous ethanol | 1.81% |
| 9 | W.S-2 | Ethanol | 2.96% |
| 10 | W.S-3 | Water | 0.35% |
| 11 | W.S-4 | 80% aqueous methanol | 1.8% |
| 12 | W.S-5 | 80% aqueous acetone | 3.1% |

Example 14: *Tinospora Cordifolia* Water Extract (T.C-1)

To dried stem powder of *Tinospora cordifolia* (100 g) was added water (250 mL), and the mixture was extracted at ambient temperature for 3 h. The mixture was filtered, and the extraction process was repeated twice with water (5×250 mL) under similar conditions. The combined water extract was evaporated under reduced pressure to give the product as a brown color solid (T.C-1; 7.5 g).

Example 15: *Tinospora Cordifolia* 50% Aqueous Ethanol Extract (T.C-2)

The 50% aqueous ethanol extract (T.C-2; 8.3 g) was obtained from 100 g raw material by adopting a similar procedure using 50% aqueous ethanol as an extraction solvent.

Example 16: *Tinospora Cordifolia* Ethanol Extract (T.C-3)

The ethanol extract (T.C-3; 2.1 g) was obtained from 100 g raw material by adopting a similar procedure using ethanol as an extraction solvent.

Example 17: Standardization of *Tinospora Cordifolia* Extracts

The various extracts of *T. cordifolia* were standardized to 8-hydroxytinosporide by the analytical HPLC method, and the results are summarized in Table 6.

TABLE 6

Details of *Tinospora cordifolia* extracts

| Example # | Extract code | Solvent for extraction | 8-hydroxytinosporide by HPLC |
|---|---|---|---|
| 14 | T.C-1 | Water | 0.25% |
| 15 | T.C-2 | 50% aqueous ethanol | 0.40% |
| 16 | T.C-3 | Ethanol | 0.55% |

Example 18: *Andrographis Paniculata* 70% Aqueous Ethanol Extract (A.P-1)

To dried whole plant powder of *Andrographis paniculata* (50 g) was added 70% aq. ethanol (300 mL), and the mixture was extracted at ambient temperature for 3 h. The mixture was filtered, and the extraction process was repeated twice with 70% aq. ethanol (2×200 mL). The combined 70% aq. ethanol layer was evaporated to minimum volume and hexane was added (50 mL). The mixture was stirred for 30 min, and the hexane layer was separated. Washing of the solution with hexane (50 mL) was repeated one more time. Then the aqueous layer was extracted with ethyl acetate (3×50 mL), and the combined ethyl acetate layer was washed with water (50 mL). The ethyl acetate layer was evaporated under reduced pressure to give the product as a green color solid (A.P-1; 1.2 g).

Example 19: *Andrographis Paniculata* Water Extract (A.P-2)

To dried whole plant powder of *Andrographis paniculata* (100 g) was added water (700 mL), and the mixture was extracted at ambient temperature for 1 h. The mixture was filtered, and the extraction process was repeated twice with water (2×500 mL) under similar conditions. The combined water extract was evaporated under reduced pressure to give the product as a pale brown color solid (A.P-2; 12.9 g).

Example 20: *Andrographis Paniculata* Ethanol Extract (A.P-3)

The ethanol extract (A.P-3; 6.9 g) was obtained from 100 g raw material by adopting a similar procedure using ethanol as an extraction solvent.

Example 21: Standardization of *Andrographis paniculata* Extracts

The various extracts of *A. paniculata* were standardized to andrographolides (sum of andrographolide, neoandrographolide, andrograpanin and 14-deoxy-11,12-didehydroandrographolide) by the analytical HPLC method, and the results are summarized in Table 7.

TABLE 7

Details of *Andrographis paniculata* extracts

| Example # | Extract code | Solvent used for extraction | Andrographolides by HPLC |
|---|---|---|---|
| 18 | A.P-1 | 70% aqueous ethanol | 33.5% |
| 19 | A.P-2 | Water | 4.33% |
| 20 | A.P-3 | Ethanol | 20.48% |

Example 22: Preparation of Various Compositions of *Terminalia Chebula* Extract Containing Zinc Salt and *Withania Somnifera* 60% Aqueous Ethanol Extract Composition-1 (C-1): The composition-1 was prepared by combining *T. chebula* extract containing zinc salt (T.Ch.Zn-1) and *W. somnifera* 60% aqueous ethanol extract (W.S-1) in the ratio of 3:1.

Composition-2 (C-2): The composition-2 was prepared by combining *T. chebula* extract containing zinc salt (T.Ch.Zn-1) and *W. somnifera* 60% aqueous ethanol extract (W.S-1) in the ratio of 2:1.

Composition-3 (C-3): The composition-3 was prepared by combining *T. chebula* extract containing zinc salt (T.Ch.Zn-1) and *W. somnifera* 60% aqueous ethanol extract (W.S-1) in the ratio of 1:1.

Composition-4 (C-4): The composition-4 was prepared by combining *T. chebula* extract containing zinc salt (T.Ch.Zn-1) and *W. somnifera* 60% aqueous ethanol extract (W.S-1) in the ratio of 1:2.

Composition-5 (C-5): The composition-5 was prepared by combining *T. chebula* extract containing zinc salt (T.Ch.Zn-1) and *W. somnifera* 60% aqueous ethanol extract (W.S-1) in the ratio of 1:3.

Composition for comparison (comp-3A): This composition-3A (C-3A) was prepared by combining *T. chebula* extract without zinc salt (T.Ch) and *W. somnifera* 60% aqueous ethanol extract (W.S-1) in the ratio of 1:1.

Example 23: Preparation of Various Compositions of *Terminalia Chebula* Enriched Extract Containing Zinc Salt and *Withania Somnifera* 60% Aqueous Ethanol Extract Composition-6 (C-6): The composition-6 was prepared by combining *T. chebula* enriched extract containing zinc salt (T.Ch.Zn-2) and *W. somnifera* 60% aqueous ethanol extract (W.S-1) in the ratio of 2:1.

Composition-7 (C-7): The composition-7 was prepared by combining *T. chebula* enriched extract containing zinc salt (T.Ch.Zn-2) and *W. somnifera* 60% aqueous ethanol extract (W.S-1) in the ratio of 1:1.

Composition-8 (C-8): The composition-8 was prepared by combining *T. chebula* enriched extract containing zinc salt (T.Ch.Zn-2) and *W. somnifera* 60% aqueous ethanol extract (W.S-1) in the ratio of 1:2.

Example 24: Preparation of Various Compositions of *Terminalia Chebula* Extract Containing Zinc Salt and *Tinospora Cordifolia* Water Extract Composition-9 (C-9): The composition-9 was prepared by combining *T. chebula* extract containing zinc salt (T.Ch.Zn-1) and *T. cordifolia* water extract (T.C-1) in the ratio of 2:1.

Composition-10 (C-11): The composition-11 was prepared by combining *T. chebula* extract containing zinc salt (T.Ch.Zn-1) and *T. cordifolia* water extract (T.C-1) in the ratio of 1:1.

Composition-11 (C-11): The composition-11 was prepared by combining *Terminalia chebula* extract containing zinc salt (T.Ch.Zn-1) and *Tinospora cordifolia* water extract (T.C-1) in the ratio of 1:2.

Example 25: Preparation of Various Compositions of *Terminalia Chebula* Extract Containing Zinc Salt and *Andrographis Paniculata* 70% Aqueous Ethanol Extract (A.P-1)

Composition-12 (C-12): The composition-12 was prepared by combining *T. chebula* extract containing zinc salt (T.Ch.Zn-1) and *A. paniculata* 70% aqueous ethanol extract (A.P-1) in the ratio of 2:1.

Composition-13 (C-13): The composition-13 was prepared by combining *T. chebula* extract containing zinc salt (T.Ch.Zn-1) and *A. paniculata* 70% aqueous ethanol extract (A.P-1) in the ratio of 1:1.

Composition-14 (C-14): The composition-14 was prepared by combining *T. chebula* extract containing zinc salt (T.Ch.Zn-1) and *A. paniculata* 70% aqueous ethanol extract (A.P-1) in the ratio of 1:2.

Example 26: Preparation of Various Compositions of *Terminalia Chebula* Extract Containing Magnesium Salt and *Withania Somnifera* Ethanol Extract Composition-15 (C-15): The composition-15 was prepared by combining *T. chebula* extract containing magnesium salt (T.Ch.Mg) and *W. somnifera* ethanol extract (W.S-2) in the ratio of 2:1.

Composition-16 (C-16): The composition-16 was prepared by combining *T. chebula* extract containing magnesium salt (T.Ch.Mg) and *W. somnifera* ethanol extract (W.S-2) in the ratio of 1:1.

Composition-17 (C-17): The composition-17 was prepared by combining *T. chebula* extract containing magnesium salt (T.Ch.Mg) and *W. somnifera* ethanol extract (W.S-2) in the ratio of 1:2.

Example 27: Preparation of Various Compositions of *Terminalia Chebula* Extract Containing Magnesium Salt and *Tinospora Cordifolia* 50% Aqueous Ethanol Extract Composition-18 (C-18): The composition-18 was prepared by combining *T. chebula* extract containing magnesium salt (T.Ch.Mg) and *T. cordifolia* 50% aqueous ethanol extract (T.C-2) in the ratio of 2:1.

Composition-19 (C-19): The composition-19 was prepared by combining *T. chebula* extract containing magnesium salt (T.Ch.Mg) and *T. cordifolia* 50% aqueous ethanol extract (T.C-2) in the ratio of 1:1.

Composition-20 (C-20): The composition-20 was prepared by combining *T. chebula* extract containing magnesium salt (T.Ch.Mg) and *T. cordifolia* 50% aqueous ethanol extract (T.C-2) in the ratio of 1:2.

Example 28: Preparation of Various Compositions of *Terminalia Chebula* Extract Containing Magnesium Salt and *Andrographis paniculata* Water Extract Composition-21 (C-21): The composition-21 was prepared by combining *T. chebula* extract containing magnesium salt (T.Ch.Mg) and *A. paniculata* water extract (A.P-2) in the ratio of 2:1.

Composition-22 (C-22): The composition-22 was prepared by combining *T. chebula* extract containing magnesium salt (T.Ch.Mg) and *A. paniculata* water extract (A.P-2) in the ratio of 1:1.

Composition-23 (C-23): The composition-23 was prepared by combining *T. chebula* extract containing magnesium salt (T.Ch.Mg) and *A. paniculata* water extract (A.P-2) in the ratio of 1:2.

Example 29: Preparation of Various Compositions of *Terminalia Chebula* Extract Containing Calcium Salt and *Withania Somnifera* 80% Aqueous Methanol Extract Composition-24 (C-24): The composition-24 was prepared by combining *T. chebula* extract containing calcium salt (T.Ch.Ca) and *W. somnifera* 80% aqueous methanol extract (W. S-4) in the ratio of 2:1.

Composition-25 (C-25): The composition-25 was prepared by combining *T. chebula* extract containing calcium salt (T.Ch.Ca) and *W. somnifera* 80% aqueous methanol extract (W. S-4) in the ratio of 1:1.

Composition-26 (C-26): The composition-26 was prepared by combining *T. chebula* extract containing calcium salt (T.Ch.Ca) and *W. somnifera* 80% aqueous methanol extract (W. S-4) in the ratio of 1:2.

Example 30: Preparation of Various Compositions of *Terminalia Chebula* Extract Containing Calcium Salt and *Tinospora cordifolia* Ethanol Extract Composition-27 (C-27): The composition-27 was prepared by combining *T. chebula* extract containing calcium salt (T.Ch.Ca) and *T. cordifolia* ethanol extract (T.C-3) in the ratio of 2:1.

Composition-28 (C-28): The composition-28 was prepared by combining *T. chebula* extract containing calcium salt (T.Ch.Ca) and *T. cordifolia* ethanol extract (T.C-3) in the ratio of 1:1.

Composition-29 (C-29): The composition-29 was prepared by combining *T. chebula* extract containing calcium salt (T.Ch.Ca) and *T. cordifolia* ethanol extract (T.C-3) in the ratio of 1:2.

Example 31: Preparation of Various Compositions of *Terminalia Chebula* Extract Containing Calcium Salt and *Andrographis Paniculata* Ethanol Extract Composition-30 (C-30): The composition-30 was prepared by combining *T. chebula* extract containing calcium salt (T.Ch.Ca) and *A. paniculata* ethanol extract (A.P-3) in the ratio of 2:1.

Composition-31 (C-31): The composition-31 was prepared by combining *T. chebula* extract containing calcium salt (T.Ch.Ca) and *A. paniculata* ethanol extract (A.P-3) in the ratio of 1:1.

Composition-32 (C-32): The composition-32 was prepared by combining *T. chebula* extract containing calcium salt (T.Ch.Ca) and *A. paniculata* ethanol extract (A.P-3) in the ratio of 1:2.

Example 32: Preparation of Various Compositions of *Terminalia Chebula* Extract Containing Potassium Salt and *Withania Somnifera* 80% Aqueous Acetone Extract Composition-33 (C-33): The composition-33 was prepared by combining *T. chebula* extract containing potassium salt (T.Ch.K) and *W. somnifera* 80% aqueous acetone extract (W.S-5) in the ratio of 2:1.

Composition-34 (C-34): The composition-34 was prepared by combining *T. chebula* extract containing potassium salt (T.Ch.K) and *W. somnifera* 80% aqueous acetone extract (W.S-5) in the ratio of 1:1.

Composition-35 (C-35): The composition-35 was prepared by combining *T. chebula* extract containing potassium salt (T.Ch.K) and *W. somnifera* 80% aqueous acetone extract (W.S-5) in the ratio of 1:2.

Example 33: Formulation of the Compositions

Composition-36 (C-36): *Terminalia chebula* extract containing zinc salt of chebulagic acid and zinc salt of chebulinic acid and zinc salt of gallic acid (45 g, T.Ch.Zn-1) was added slowly to water (100 mL) at RT, under stirring for 20-30 min to get a homogenous solution. Then successively added ultrasperse-A (3 g) and glucidex (5 g) to the suspension and continue the stirring for 10-15 min. A solution of *Withania somnifera* 60% aqueous ethanol extract (45 g, W.S-1) in 60% aqueous ethanol (100 mL) was added slowly to the above suspension and stirring was continued for 20-30 min. The resultant slurry was dried under vacuum to give the composition as flakes. These flakes are homogeneously blended with colloidal silicon dioxide (2 g) in a polyethylene cover or any suitable blender and pulverized the material to give the composition as a fine powder (comp-36).

Example 34: Assay for Interleukin-2 (IL-2) Production

In a 96-well plate, an equal number of Jurkat cells ($0.1\times10^6$ cells/well) was seeded with 200 μL of RPMI medium supplemented with 10% FBS. Cells were pretreated with different concentrations of test samples. Cells with 0.2% DMSO served as vehicle control. The plate was incubated in a $CO_2$ incubator at 37° C. for 2 hrs. After due incubation, the cells were induced with the combination of Phorbol-12-myristate-13-acetate (PMA, 7.5 nM) and Phytohemagglutinin-A (PHA, 0.5 μg/ml) for 4 hours except for vehicle control by keeping the plate at 37° C. in a $CO_2$ incubator. The plate was centrifuged at 270×g for 5 minutes, and cell-free culture supernatants were collected. Quantitation of IL-2 was performed using the ELISA kit (R&D systems Cat #DY202) according to the manufacturer's instructions. Absorbance was measured at 450 nm in a Spectramax2e plate reader. The percent increase in IL-2 production was calculated using the following formula.

$$\%\text{ increase in } IL\text{-}2 \text{ production} = \frac{(Concn.\text{ of } IL\text{-}2 \text{ in Test Sample}) - (Cocn.\text{ of } IL\text{-}2 \text{ in Induction})}{(Concn.\text{ of } IL\text{-}2 \text{ in Induction})} \times 100$$

The results are presented in Tables: 8-12.

TABLE 8

Percent increasein IL-2 production by the compositions of *Terminalia chebula* extract containing zinc salt (T.Ch.Zn-1) and *Withania somnifera* 60% aqueous ethanol extract (W.S-1); compositions of *T. chebula* enriched extract containing zinc salt (T.Ch.Zn-2) and *Withania somnifera* 60% aqueous ethanol extract (W.S-1)

| | | | | | | | % Increase in IL-2 production | |
|---|---|---|---|---|---|---|---|---|
| Comp # | μg/mL | % increase | μg/mL | % increase | Ratio | Dose μg/mL | Additive (Calculated) | Observed |
| | T.Ch.Zn-1 | | W.S-1 | | | | | |
| C-1 | 7.5 | 15.50 | 2.5 | 5.83 | 3:1 | 10 | 21.33 | 31.04 |
| C-2 | 6.67 | 13.79 | 3.33 | 7.77 | 2:1 | 10 | 21.56 | 33.59 |
| C-3 | 5.0 | 10.34 | 5.0 | 11.67 | 1:1 | 10 | 22.00 | 39.78 |
| C-4 | 3.33 | 6.88 | 6.67 | 15.56 | 1:2 | 10 | 22.44 | 36.51 |
| C-5 | 2.5 | 5.17 | 7.5 | 17.50 | 3:1 | 10 | 22.67 | 34.48 |
| | T.Ch.Zn-2 | | W.S-1 | | | | | |
| C-6 | 6.67 | 10.02 | 3.33 | 7.77 | 2:1 | 10 | 17.79 | 26.46 |
| C-8 | 3.33 | 5.00 | 6.67 | 15.56 | 1:2 | 10 | 20.56 | 29.93 |

TABLE 9

Percent increase in IL-2 production by the compositions of *T. chebula* extract containing zinc salt (T.Ch.Zn-1) and *T. cordifolia* water extract (T.C-1) or *A. paniculata* 70% aqueous ethanol extract (A.P-1)

| | | | | | | | % Increase in IL-2 production | |
|---|---|---|---|---|---|---|---|---|
| Comp # | μg/mL | % increase | μg/mL | % increase | Ratio | Dose μg/mL | Additive (Calculated) | Observed |
| | T.Ch.Zn-1 | | T.C-1 | | | | | |
| C-9 | 6.67 | 13.79 | 3.33 | 3.10 | 2:1 | 10 | 16.88 | 23.85 |
| C-10 | 5.0 | 10.34 | 5.0 | 4.65 | 1:1 | 10 | 14.99 | 23.38 |
| | T.Ch.Zn-1 | | A.P-1 | | | | | |
| C-12 | 6.67 | 13.79 | 3.33 | 3.39 | 2:1 | 10 | 17.18 | 24.8 |
| C-14 | 3.33 | 6.88 | 6.67 | 6.80 | 1:2 | 10 | 13.68 | 21.67 |

TABLE 10

Percent increase in IL-2 production by the compositions of *T. chebula* extract containing magnesium salt (T.Ch.Mg) and *W. somnifera* ethanol extract (W.S-2) or *T. cordifolia* 50% aqueous ethanol extract (T.C-2) or *A. paniculata* water extract (A.P-2)

| Comp # | μg/mL | % increase | μg/mL | % increase | Ratio | Dose μg/mL | % Increase in IL-2 production Additive (Calculated) | % Increase in IL-2 production Observed |
|---|---|---|---|---|---|---|---|---|
| | T.Ch.Mg | | W.S-2 | | | | | |
| C-15 | 6.67 | 6.60 | 3.33 | 3.50 | 2:1 | 10 | 10.09 | 18.85 |
| C-17 | 3.33 | 3.29 | 6.67 | 7.00 | 1:2 | 10 | 10.30 | 15.55 |
| | T.Ch.Mg | | T.C-2 | | | | | |
| C-18 | 6.67 | 6.60 | 3.33 | 5.19 | 2:1 | 10 | 11.79 | 18.85 |
| C-20 | 3.33 | 3.29 | 6.67 | 10.41 | 1:2 | 10 | 13.70 | 21.9 |
| | T.Ch.Mg | | A.P-2 | | | | | |
| C-21 | 6.67 | 6.60 | 3.33 | 4.73 | 2:1 | 10 | 11.33 | 16.23 |
| C-23 | 3.33 | 3.29 | 6.67 | 9.48 | 1:2 | 10 | 12.77 | 23.67 |

TABLE 11

Percent increase in IL-2 production by the compositions of *T. chebula* extract containing calcium salt (T.Ch.Ca) and *W. somnifera* 80% aqueous methanol extract (W.S-4) or *T. cordifolia* ethanol extract (T.C-3) or *A. paniculata* ethanol extract (A.P-3)

| Comp # | μg/mL | % increase | μg/mL | % increase | Ratio | Dose μg/mL | % Increase in IL-2 production Additive (Calculated) | % Increase in IL-2 production Observed |
|---|---|---|---|---|---|---|---|---|
| | T.Ch.Ca | | W.S-4 | | | | | |
| C-24 | 6.67 | 11.04 | 3.33 | 5.18 | 2:1 | 10 | 16.22 | 24.84 |
| C-26 | 3.33 | 5.51 | 6.67 | 10.37 | 1:2 | 10 | 15.88 | 21.03 |
| | T.Ch.Ca | | T.C-3 | | | | | |
| C-27 | 6.67 | 11.04 | 3.33 | 3.14 | 2:1 | 10 | 14.18 | 21.03 |
| C-29 | 3.33 | 5.51 | 6.67 | 6.29 | 1:2 | 10 | 11.80 | 20.13 |
| | T.Ch.Ca | | A.P-3 | | | | | |
| C-30 | 6.67 | 11.04 | 3.33 | 4.20 | 2:1 | 10 | 15.24 | 26.28 |
| C-32 | 3.33 | 5.51 | 6.67 | 8.41 | 1:2 | 10 | 13.92 | 18.26 |

TABLE 12

Percent increase in IL-2 production by the compositions of *T. chebula* extract containing potassium salt (T.Ch.K) and *W. somnifera* 80% aqueous acetone extract (W.S-5)

| | T.Ch.K | | W.S-5 | | | | % Increase in IL-2 production | |
|---|---|---|---|---|---|---|---|---|
| Comp # | μg/mL | % increase | μg/mL | % increase | Ratio | Dose μg/mL | Additive (Calculated) | Observed |
| C-33 | 6.67 | 9.46 | 3.33 | 6.23 | 2:1 | 10 | 15.69 | 21.12 |
| C-35 | 3.33 | 4.72 | 6.67 | 12.48 | 1:2 | 10 | 17.20 | 30.91 |

Example 35: Assay for Interferon-γ (IFN-γ) Production

Human blood was collected from healthy volunteers from a peripheral vein with a syringe containing EDTA at a final concentration of 2 mM. Plasma was separated by centrifugation at 150×g for 10 minutes, and the residual blood was diluted with RPMI medium supplemented with 10% FBS and 2 mM EDTA in a ratio of 1:3. Thirty milliliters of blood was carefully layered onto 15 mL of Ficoll/Lymphoprep in a 50 mL falcon tube in the dark, and tubes were centrifuged at 350×g for 30 minutes at an acceleration of 9 without using a brake. Buffy coat (interface between medium and Ficoll) containing peripheral blood mononuclear cells (PBMC) was collected carefully in 25 mL of cold 1× phosphate-buffered saline (PBS) and centrifuged at 1200 rpm for 10 minutes.

Residual RBCs found in PBMCs pellet were removed by treating with ACK lysis buffer (Gibco, USA; Cat #A10492-01) and washed with fresh 1×PBS. PBMC were seeded in a 96-well plate with a density of $0.1\times10^6$ cells/well and treated with different concentrations of test samples. Cells with 0.2% DMSO served as vehicle control. The plate was incubated in a $CO_2$ incubator at 37° C. for 2 hrs. Finally, cells were induced with the combination of Phorbol-12-myristate-13-acetate (PMA, 7.5 nM) and Phytohemagglutinin-A (PHA, 2 µg/ml) for 4 hours except for vehicle control by keeping the plate at 37° C. in a $CO_2$ incubator. The plate was centrifuged at 270×g for 5 minutes, and 120 µL of cell-free supernatants were collected. Quantification of IFN-γ was performed using the ELISA kit (R&D Systems Cat #DY285) according to the manufacturer's instructions. Absorbance was measured at 450 nm in a Spectramax2e plate reader. The percent increase in IFN-γ production was calculated using the following formula.

$$\%\text{ increase in } INF-\gamma \text{ production} = \frac{(IFN-\gamma\ concn.\text{ in Test Sample}) - (IFN-\gamma\ concn.\text{ in Induction})}{(IFN-\gamma\ concn.\text{ in Induction})} \times 100$$

The results are presented in Tables: 13-17.

TABLE 13

Percent increase in IFN-γ production by the compositions of *Terminalia chebula* extract containing zinc salt (T.Ch.Zn-1) and *Withania somnifera* 60% aqueous ethanol extract (W.S-1); compositions of *T. chebula* enriched extract containing zinc salt (T.Ch.Zn-2) and *W. somnifera* 60% aqueous ethanol extract (W.S-1)

| Comp # | µg/mL | % increase | µg/mL | % increase | Ratio | Dose µg/mL | % Increase in IFN-γ production: Additive (Calculated) | % Increase in IFN-γ production: Observed |
|---|---|---|---|---|---|---|---|---|
| | T.Ch.Zn-1 | | W.S-1 | | | | | |
| C-1 | 7.5 | 13.77 | 2.5 | 5.26 | 3:1 | 10 | 19.03 | 24.96 |
| C-2 | 6.67 | 12.25 | 3.33 | 7.00 | 2:1 | 10 | 19.25 | 30.86 |
| C-3 | 5.0 | 9.18 | 5.0 | 10.52 | 1:1 | 10 | 19.70 | 41.08 |
| C-4 | 3.33 | 6.11 | 6.67 | 14.03 | 1:2 | 10 | 20.14 | 32.79 |
| C-5 | 2.5 | 4.59 | 7.5 | 15.77 | 1:3 | 10 | 20.36 | 34.76 |
| | T.Ch.Zn-2 | | W.S-1 | | | | | |
| C-7 | 5.0 | 7.36 | 5.0 | 10.52 | 1:1 | 10 | 17.87 | 25.5 |
| C-8 | 3.33 | 4.90 | 6.67 | 14.03 | 1:2 | 10 | 18.93 | 26.58 |

TABLE 14

Percent increase in IFN-γ production by the compositions of *T. chebula* extract containing zinc salt (T.Ch.Zn-1) and *T. cordifolia* water extract (T.C-1) or *A. paniculata* 70% aqueous ethanol extract (A.P-1)

| Comp # | µg/mL | % increase | µg/mL | % increase | Ratio | Dose µg/mL | % Increase in IFN-γ production: Additive (Calculated) | % Increase in IFN-γ production: Observed |
|---|---|---|---|---|---|---|---|---|
| | T.Ch.Zn-1 | | T.C-1 | | | | | |
| C-9 | 6.67 | 12.25 | 3.33 | 4.58 | 2:1 | 10 | 16.82 | 24.2 |
| C-11 | 3.33 | 6.11 | 6.67 | 9.16 | 1:2 | 10 | 15.28 | 21.29 |
| | T.Ch.Zn-1 | | A.P-1 | | | | | |
| C-12 | 6.67 | 12.25 | 3.33 | 3.32 | 2:1 | 10 | 15.57 | 22.17 |
| C-14 | 3.33 | 6.11 | 6.67 | 6.65 | 1:2 | 10 | 12.76 | 24.92 |

TABLE 15

Percent increase in IFN-γ production by the compositions of *T. chebula* extract containing magnesium salt (T.Ch.Mg) and *W. somnifera* ethanol extract (W.S-2) or *T. cordifolia* 50% aqueous ethanol extract (T.C-2) or *A. paniculata* water extract (A.P-2)

| Comp # | μg/mL | % increase | μg/mL | % increase | Ratio | Dose μg/mL | % Increase in IFN-γ production Additive (Calculated) | Observed |
|---|---|---|---|---|---|---|---|---|
| | T.Ch.Mg | | W.S-2 | | | | | |
| C-15 | 6.67 | 9.93 | 3.33 | 3.27 | 2:1 | 10 | 13.20 | 17.94 |
| C-17 | 3.33 | 4.96 | 6.67 | 6.54 | 1:2 | 10 | 11.50 | 19.78 |
| | T.Ch.Mg | | T.C-2 | | | | | |
| C-18 | 6.67 | 9.93 | 3.33 | 3.29 | 2:1 | 10 | 13.23 | 19.87 |
| C-20 | 3.33 | 4.96 | 6.67 | 6.60 | 1:2 | 10 | 11.56 | 23.34 |
| | T.Ch.Mg | | A.P-2 | | | | | |
| C-21 | 6.67 | 9.93 | 3.33 | 5.62 | 2:1 | 10 | 15.55 | 18.24 |
| C-23 | 3.33 | 4.96 | 6.67 | 11.25 | 1:2 | 10 | 16.21 | 20.46 |

TABLE 16

Percent increase in IFN-γ production by the compositions of *T. chebula* extract containing calcium salt (T.Ch.Ca) and *W. somnifera* 80% aqueous methanol extract (W.S-4) or *T. cordifolia* ethanol extract (T.C-3) or *A. paniculata* ethanol extract (A.P-3)

| Comp # | μg/mL | % increase | μg/mL | % increase | Ratio | Dose μg/mL | % Increase in IFN-γ production Additive (Calculated) | Observed |
|---|---|---|---|---|---|---|---|---|
| | T.Ch.Ca | | W.S-4 | | | | | |
| C-24 | 6.67 | 8.93 | 3.33 | 5.95 | 2:1 | 10 | 14.88 | 26.28 |
| C-26 | 3.33 | 4.46 | 6.67 | 11.91 | 1:2 | 10 | 16.37 | 21.87 |
| | T.Ch.Ca | | T.C-3 | | | | | |
| C-27 | 6.67 | 8.93 | 3.33 | 2.72 | 2:1 | 10 | 11.65 | 19.86 |
| C-29 | 3.33 | 4.46 | 6.67 | 5.44 | 1:2 | 10 | 9.90 | 14.47 |
| | T.Ch.Ca | | A.P-3 | | | | | |
| C-31 | 5.0 | 6.70 | 5.0 | 7.88 | 1:1 | 10 | 14.57 | 26.46 |
| C-32 | 3.33 | 4.46 | 6.67 | 10.51 | 1:2 | 10 | 14.96 | 21.97 |

TABLE 17

The percent increase in IFN-γ production by the compositions of *T. chebula* extract containing potassium salt (T.Ch.K) and *W. somnifera* 80% aqueous acetone extract (W.S-5)

| | T.Ch.K | | W.S-5 | | | | % Increase in IFN-γ production | |
|---|---|---|---|---|---|---|---|---|
| Comp # | μg/mL | % increase | μg/mL | % increase | Ratio | Dose μg/mL | Additive (Calculated) | Observed |
| C-34 | 5.0 | 5.26 | 5.0 | 3.95 | 1:1 | 10 | 9.20 | 12.72 |
| C-35 | 3.33 | 3.50 | 6.67 | 5.26 | 1:2 | 10 | 8.76 | 16.36 |

Example 36: Assay for Lymphocyte Proliferation

An equal number of human peripheral blood mononuclear cells (PBMC; $0.1\times10^6$) was seeded in each well of a 96-well plate and treated with different concentrations of the test samples for 72 hrs in a $CO_2$ incubator at 37° C. At the end of the incubation period, the cells were treated again with the respective concentrations of the test samples for 5 hrs at 37° C. in a $CO_2$ incubator. The cells incubated with 0.2% DMSO served as the vehicle control. The treatment plate was centrifuged at 180 g for 10 minutes, and the cell pellet was collected in FACS buffer, transferred into a 'v' bottom 96-well plate, and processed for flow cytometry staining. Intracellular staining was performed using a BD Cytofix/Cytoperm™ Plus Fixation/Permeabilization Kit (with BD GolgiPlug™ protein transport inhibitor-containing brefeldin A (BD Biosciences Cat #555028) following the manufacturer's protocol. Alexa Fluor® 488 anti-mouse/human Ki67 antibody (Cat #151204; Biolegend) was used to detect Ki67 expression. Finally, the cells were suspended in staining buffer and acquired in a BD FACSVerse flow cytometer for Ki67 positive cells. The percent increase of lymphocyte proliferation in the test samples treated wells was calculated using the following formula.

$$\%\text{ increase in lymphocyte proliferation} = \frac{(\%\ Ki67+ve\text{ cells in Test Sample}) - (\%\ Ki67+ve\text{ cells in Control})}{(\%\ Ki67+ve\text{ cells in Control})} \times 100$$

The results are presented in Tables: 18-21.

TABLE 18

Percent increase in lymphocyte proliferation by the compositions of *Terminalia chebula* extract containing zinc salt (T.Ch.Zn-1) and *Withania somnifera* 60% aqueous ethanol extract (W.S-1); compositions of *T. chebula* enriched extract containing zinc salt (T.Ch.Zn-2) and *W. somnifera* 60% aqueous ethanol extract (W.S-1)

| Comp # | μg/mL | % increase | μg/mL | % increase | Ratio | Dose μg/mL | % Increase in lymphocyte proliferation Additive (Calculated) | Observed |
|---|---|---|---|---|---|---|---|---|
| | T.Ch.Zn-1 | | W.S-1 | | | | | |
| C-1 | 7.5 | 10.04 | 2.5 | 4.21 | 3:1 | 10 | 14.25 | 20.03 |
| C-2 | 6.67 | 8.92 | 3.33 | 5.61 | 2:1 | 10 | 14.54 | 19.49 |
| C-3 | 5.0 | 6.69 | 5.0 | 8.43 | 1:1 | 10 | 15.12 | 24.03 |
| C-4 | 3.33 | 4.46 | 6.67 | 11.24 | 1:2 | 10 | 15.69 | 21.13 |
| C-5 | 2.5 | 3.35 | 7.5 | 12.64 | 3:1 | 10 | 15.98 | 21.04 |
| | T.Ch.Zn-2 | | W.S-1 | | | | | |
| C-6 | 6.67 | 8.48 | 3.33 | 5.61 | 2:1 | 10 | 14.10 | 18.29 |
| C-8 | 3.33 | 4.24 | 6.67 | 11.24 | 1:2 | 10 | 15.47 | 20.09 |

TABLE 19

Percent increase in lymphocyte proliferation by the compositions of *T. chebula* extract containing zinc salt (T.Ch.Zn-1) and *T. cordifolia* water extract (T.C-1) or *A. paniculata* 70% aqueous ethanol extract (A.P-1)

| Comp # | μg/mL | % increase | μg/mL | % increase | Ratio | Dose μg/mL | % Increase in lymphocyte proliferation Additive (Calculated) | Observed |
|---|---|---|---|---|---|---|---|---|
| | T.Ch.Zn-1 | | T.C-1 | | | | | |
| C-10 | 5.0 | 6.69 | 5.0 | 3.14 | 1:1 | 10 | 9.83 | 18.05 |
| C-11 | 3.33 | 4.46 | 6.67 | 4.18 | 1:2 | 10 | 8.64 | 12.95 |
| | T.Ch.Zn-1 | | A.P-1 | | | | | |
| C-13 | 5.0 | 6.69 | 5.0 | 3.73 | 1:1 | 10 | 10.42 | 18.23 |
| C-14 | 3.33 | 4.46 | 6.67 | 4.98 | 1:2 | 10 | 9.43 | 18.55 |

TABLE 20

Percent increase in lymphocyte proliferation by the compositions of *T. chebula* extract containing magnesium salt (T.Ch.Mg) and *W. somnifera* ethanol extract (W.S-2) or *T. cordifolia* 50% aqueous ethanol extract (T.C-2) or *A. paniculata* water extract (A.P-2)

| Comp # | μg/mL | % increase | μg/mL | % increase | Ratio | Dose μg/mL | % Increase in lymphocyte proliferation Additive (Calculated) | Observed |
|---|---|---|---|---|---|---|---|---|
| | T.Ch.Mg | | W.S-2 | | | | | |
| C-15 | 6.67 | 7.26 | 3.33 | 2.16 | 2:1 | 10 | 9.42 | 11.39 |
| C-17 | 3.33 | 3.63 | 6.67 | 4.32 | 1:2 | 10 | 7.95 | 13.47 |

TABLE 20-continued

Percent increase in lymphocyte proliferation by the compositions of *T. chebula* extract containing magnesium salt (T.Ch.Mg) and *W. somnifera* ethanol extract (W.S-2) or *T. cordifolia* 50% aqueous ethanol extract (T.C-2) or *A. paniculata* water extract (A.P-2)

| Comp # | μg/mL | % increase | μg/mL | % increase | Ratio | Dose μg/mL | % Increase in lymphocyte proliferation Additive (Calculated) | Observed |
|---|---|---|---|---|---|---|---|---|
| | T.Ch.Mg | | T.C-2 | | | | | |
| C-18 | 6.67 | 7.26 | 3.33 | 1.50 | 2:1 | 10 | 8.76 | 11.15 |
| C-20 | 3.33 | 3.63 | 6.67 | 3.00 | 1:2 | 10 | 6.63 | 13.27 |
| | T.Ch.Mg | | A.P-2 | | | | | |
| C-22 | 5.0 | 5.45 | 5.0 | 4.60 | 1:1 | 10 | 10.04 | 15.64 |
| C-23 | 3.33 | 3.63 | 6.67 | 6.13 | 1:2 | 10 | 9.76 | 14.34 |

TABLE 21

Percent increase in lymphocyte proliferation by the compositions of *T. chebula* extract containing calcium salt (T.Ch.Ca) and *W. somnifera* 80% aqueous methanol extract (W.S-4) or *T. cordifolia* ethanol extract (T.C-3) or *A. paniculata* ethanol extract (A.P-3)

| Comp # | μg/mL | % increase | μg/mL | % increase | Ratio | Dose μg/mL | % Increase in lymphocyte proliferation Additive (Calculated) | Observed |
|---|---|---|---|---|---|---|---|---|
| | T.Ch.Ca | | W.S-4 | | | | | |
| C-24 | 6.67 | 6.52 | 3.33 | 3.14 | 2:1 | 10 | 9.66 | 13.50 |
| C-26 | 3.33 | 3.26 | 6.67 | 6.28 | 1:2 | 10 | 9.54 | 14.20 |
| | T.Ch.Ca | | T.C-3 | | | | | |
| C-27 | 6.67 | 6.52 | 3.33 | 3.78 | 2:1 | 10 | 10.31 | 15.72 |
| C-29 | 3.33 | 3.26 | 6.67 | 7.58 | 1:2 | 10 | 10.83 | 16.60 |
| | T.Ch.Ca | | A.P-3 | | | | | |
| C-31 | 5.0 | 4.89 | 5.0 | 7.53 | 1:1 | 10 | 12.42 | 18.62 |
| C-32 | 3.33 | 3.26 | 6.67 | 10.04 | 1:2 | 10 | 13.30 | 21.29 |

Example 37: In-vivo Study of Modulation of Inflammation and Immune Response in Rats Modulations of inflammation and immune response by the test samples were evaluated in bacterial lipopolysaccharide (LPS from *Escherichia coli O*111:B4; Merck Cat #L2630-25MG) induced acute lung injury model in 8-9 weeks old male BALB/c mice of body weight between 25 and 30 grams. The animals were randomly allocated into five groups. Each group contained eight animals (n=8). The animals in each group received oral supplementation of either 0.5% carboxymethyl cellulose (CMC) or the test items for seven days. Groups 1 and 2 (G1 and G2) received CMC; groups 3 (G3), 4 (G4), and 5 (G5) received W.S-1, T.Ch.Zn-1, and comp-36 at 100 mg/kg body weight (BW), respectively. On day 7, each animal, except the G1, received an intraperitoneal (i.p.) dose of LPS (5 mg/kg BW) after 1 hour of the vehicle/test item administration. The G1 animals received an i.p. administration of sterile phosphate-buffered saline (PBS). After eight hours of LPS induction, the blood samples were collected from each mouse using retro-orbital puncture under mild anesthesia. Then, the animals were euthanized using an overdose of thiopentone sodium, followed by exsanguination, and subjected to necropsy. The spleens were collected to analyze immune cells using flow cytometry (FACS). Serum biomarkers were measured from the blood samples.

Biomarker analysis (IL-6 and total IgG): IL-6 and total IgG in the serum samples from the experimental animals were measured using IL-6 (Merck Cat #RAB0308) and total IgG (AbCam Cat #ab157719) enzyme-linked immunosorbent assay (ELISA) kits, respectively. The assay procedures followed the manufacturer's protocols. Briefly, 100 μL of the serum samples or standards were added to each well of the pre-coated 96-well ELISA plates and incubated for 2.5 hours at room temperature. After the incubation, the plates were washed with 1× wash buffer. To each well, 100 μL of detection antibody was added and incubated for 1 hour at room temperature with gentle shaking. The washing step was repeated, and 100 μL of Streptavidin solution was added; the plate was sealed and incubated for 45 minutes at room temperature with gentle shaking. After wash, TMB substrate was added; plates were sealed and incubated for 30 minutes in the dark at room temperature with gentle shaking. Fifty microliters of stop solution were added, and absorbance was measured at 450 nm in a microplate reader (Spectramax2e; Molecular Devices, San Jose, CA). The levels of IL-6 and total IgG were quantified utilizing a standard curve generated for each analyte.

Immune cell population in Spleen cell preparation: The spleens of the experimental mice were gently crushed on Falcon® 100 μm sterile cell strainers (Corning, Cat #352360) using 1×RPMI medium to obtain a single cell suspension of splenocytes. The number of splenocytes was counted, and $0.3\times10^{6}$ cells were taken into a 'v' bottom 96-well plate using FACS buffer and processed for flow cytometry staining. Briefly, the cells were washed with FACS buffer and incubated with 0.3 μg of FITCanti-mouse CD3 Antibody (Biolegend, Cat #100204), 70 ng of PE anti-mouse CD4 Antibody (Biolegend, Cat #100408), and 70 ng of APC anti-mouse CD8a Antibody (Biolegend, Cat #100712) for 30 minutes in the dark at room temperature. After the incubation, the cells were washed with FACS buffer and fixed using 100 μL of BD Cytofix™ Fixation Buffer (BD Biosciences, Cat #554655) for 20 minutes in the dark. After incubation, the cells were washed with FACS buffer and resuspended in the same buffer, and acquired on BD FACSVerse flow cytometer for analysis. Percentages of the CD3, CD4, and CD8 positive cell populations in the spleen cell preparations were recorded.

The results are presented in Tables: 22-24.

TABLE 22

Percent increase in $CD3^+$ population by *Withania somnifera* 60% aqueous ethanol extract (W.S-1), *Terminalia chebula* extract containing zinc (T.Ch.Zn-1) and their composition in 1:1 ratio

| Test sample | Mean $CD3^+$ population (%) | Relative population of $CD3^+$ wrt control | % increase from LPS control |
|---|---|---|---|
| Control (G1) | 36.4 | 100 | NA |
| LPS (G2) | 32.1 | 88 | NA |
| LPS + W.S-1 (G3) | 34.6 | 95.1 | 7.79 |
| LPS + T.Ch.Zn-1 (G4) | 34.4 | 94.5 | 7.17 |
| LPS + Comp-36 (G5) | 37.4 | 102.8 | 16.51 |

TABLE 23

Percent increase in $CD4^+$ + $CD8^+$ population by *Withania somnifera* 60% aqueous ethanol extract (W.S-1), *Terminalia chebula* extract containing zinc (T.Ch.Zn-1) and their composition in 1:1 ratio

| Test sample | Mean $CD4^+$ + $CD8^+$ population (%) | Relative population of $CD4^+$ + $CD8^+$ wrt control | % increase from LPS control |
|---|---|---|---|
| Control (G1) | 31.0 | 100 | NA |
| LPS (G2) | 26.1 | 84.1 | NA |
| LPS + W.S-1 (G3) | 28.2 | 91.1 | 8.05 |
| LPS + T.Ch.Zn-1 (G4) | 28.0 | 90.3 | 7.28 |
| LPS + Comp-36 (G5) | 30.9 | 99.7 | 18.39 |

TABLE 24

Percent decrease in IL-6 and percent increase of IgG by *Withania somnifera* 60% aqueous ethanol extract (W.S-1), *Terminalia chebula* extract containing zinc (T.Ch.Zn-1), and their composition in 1:1 ratio

| Test sample | IL-6 (pg/mL) | % decrease in IL-6 from LPS induction (G2) | IgG (mg/mL) | % increase in IgG from LPS induction (G2) |
|---|---|---|---|---|
| Control (G1) | 174.7 | NA | 2.36 | NA |
| LPS (G2) | 2596.1 | NA | 1.68 | NA |
| LPS + W.S-1 (G3) | 2120.8 | 18.3 | 1.83 | 8.93 |
| LPS + T.Ch.Zn-1 (G4) | 2192.8 | 15.5 | 1.79 | 6.55 |
| LPS + Comp-36 (G5) | 1833.2 | 29.4 | 1.95 | 16.07 |

We claim:

1. An herbal composition for stimulating an immune response in a patient in need thereof, comprising:
10% to 90% by weight of a first ingredient comprising a *Terminalia chebula* extract containing a metal salt, a metal complex, or a metal chelate of a phytochemical selected from the group consisting of chebulagic acid, chebulinic acid, gallic acid, and a mixture thereof; and
10% to 90% by weight of a second ingredient comprising an extract of an herb selected from the group consisting of *Withania somnifera, Tinospora cordifolia, Andrographis paniculata*, and mixtures thereof;
wherein percentages of the first ingredient and the second ingredient are based on the combined weight of the first ingredient and the second ingredient; and
wherein the first ingredient and the second ingredient act synergistically in the patient to cause at least one of the following:
an increase in IL-2 production;
a decrease in IL-6 production;
an increase in interferon-γ production;
an increase in lymphocyte proliferation;
an increase in immune cell populations; and
an increase in IgG production.

2. The herbal composition as claimed in claim 1, wherein the *Terminalia chebula* extract contains:
the metal salt, wherein the metal salt is a salt of zinc, magnesium, calcium, or potassium;
the metal complex, wherein the metal complex is a complex of zinc, magnesium, calcium, or potassium; or
the metal chelate, wherein the metal chelate is a chelate of zinc, magnesium, calcium, or potassium.

3. The herbal composition as claimed in claim 1, wherein the herbal composition comprises 33% to 75% by weight of the first ingredient and 25% to 67% by weight of the second ingredient, based on the combined weight of the first ingredient and the second ingredient.

4. The herbal composition as claimed in claim 1, wherein the first ingredient comprises:
1.0% to 40% by weight of chebulagic acid;
1.0% to 30% by weight of chebulinic acid;
1.0% to 10% by weight of gallic acid; and
0.5-5.0% by weight of a metal ion present in the metal salt, the metal complex, or the metal chelate;
based on the weight of the first ingredient.

5. The herbal composition as claimed in claim 1, wherein the second ingredient comprises an extract of *Withania somnifera*, and
the extract of *Withania somnifera* comprises 0.01% to 10% by weight of total withanolides, 0.01% to 5% of 8-hydroxytinosporide, and 1.00% to 40% by weight of andrographolides.

6. The herbal composition as claimed in claim 1, wherein the first ingredient and the second ingredient are obtained from a plant part selected from the group consisting of a leaf, a stem, a twig, aerial parts, a whole fruit, a fruit peel rind, a seed, a flower head, a root, a bark, hardwood, a rhizome, a whole plant, and a mixture thereof.

7. The herbal composition as claimed in claim 6, wherein the first ingredient and the second ingredient are obtained from the plant part by extraction with a solvent selected from the group consisting of C1-C5 alcohols, ketones, chlorinated solvents, water, C1-C7 hydrocarbons, esters, and a mixture thereof.

8. The herbal composition as claimed in claim 6, wherein the first ingredient and the second ingredient are obtained from the plant part by extraction with a solvent selected from the group consisting of ethanol, methanol, n-propanol, isopropyl alcohol, acetone, methylisobutyl ketone, methylene dichloride, chloroform, water, hexane; ethyl acetate, and mixtures thereof.

9. The herbal composition as claimed in claim 1, further comprising a pharmaceutically, nutraceutically, or dietically acceptable excipient, carrier, or diluent.

10. The herbal composition as claimed in claim 9, wherein the excipient, carrier, or diluent is selected from the group consisting of monosaccharides, disaccharides, polycarbohydrates, dextrins, polyhydric alcohols, sugar alcohols, cellulose derivatives, silicates, metallic stearates, organic acids, fatty acid esters, esters of polysorbate, natural gums, B group vitamins, nicotinamide, calcium pantothenate, amino acids, proteins, organic metal salts, natural pigments, flavors, class I & class II preservatives, and a mixture thereof.

11. The herbal composition as claimed in claim 9, wherein the excipient, carrier, or diluent is selected from the group consisting of glucose, dextrose, fructose, galactose, sucrose, maltose, lactose, lactulose, trehalose, cellobiose, chitobiose, starch, modified starch, sodium starch glycolate, pre-gelatinized starch, soluble starch, yellow dextrin, white dextrin, maltodextrin, sorbitol, mannitol, inositol, xylitol, isomalt, microcrystalline cellulose, hydroxypropyl methyl cellulose, hydroxyethyl cellulose, veegum, talc, colloidal silicon dioxide, calcium stearate, magnesium stearate, zinc stearate, citric acid, tartaric acid, malic acid, succinic acid, lactic acid, L-ascorbic acid, fatty acid esters, polysorbate esters, acacia gum, carrageenan gum, guar gum, xanthan gum, nicotinamide, calcium pantothenate, amino acids, casein, gelatin, pectin, agar, sodium chloride, calcium chloride, dicalcium phosphate, zinc sulphate, zinc chloride, natural pigments, flavors, class I & class II preservatives, aqueous, alcoholic, hydro-alcoholic, or organic solutions thereof; and mixtures thereof.

12. The herbal composition as claimed in claim 1, wherein the herbal composition is formulated into a dosage form selected from the group consisting of a dry powder form, a liquid form, a beverage, a food product, a dietary supplement, a tablet, a capsule, a soft chewable tablet, and a gummy bear.

13. The herbal composition as claimed in claim 1, wherein the herbal composition is formulated into a tablet comprising a controlled release coating.

14. A process for preparing the herbal composition according to claim 1, wherein the process comprises the following steps of;

(i) extracting dried *Terminalia chebula* fruit powder with a solvent to obtain a solution;

(ii) treating the solution with a compound of zinc, magnesium, calcium, or potassium;

(iii) filtering the solution;

(iv) evaporating the solution and drying the residue to obtain the first ingredient;

(v) blending the first ingredient with the second ingredient; and (vi) drying the product of step (v) under vacuum to get the herbal composition.

15. The process as claimed in claim 14, wherein the solvent is selected from the group consisting of C1-C5 alcohols, water, and a mixture thereof.

16. The process as claimed in claim 14, wherein the compound of zinc, magnesium, calcium, or potassium is selected from the group consisting of zinc oxide, zinc carbonate, zinc hydroxide, magnesium oxide, magnesium carbonate, magnesium hydroxide, calcium hydroxide, calcium carbonate, potassium hydroxide, and potassium carbonate.

17. A method of stimulating an immune response in a patient in need thereof, wherein the method comprises administering the herbal composition of claim 1 to the patient.

18. A method of stimulating an immune response in a patient in need thereof, wherein the method comprises administering the herbal composition of claim 1 to the patient, wherein stimulating an immune response comprises at least one of:

eliciting an immune response in the patient;

improving innate immunity in the patient;

improving adaptive immunity in the patient;

improving cellular immunity in the patient;

improving humoral immunity in the patient;

improving protection from airway inflammation in the patient;

improving protection from microbial infection in the patient;

treating viral respiratory infections in the patient; and improving respiratory health in the patient.

19. An herbal composition comprising:

33% to 75% by weight of a first ingredient comprising a reaction product of:

a *Terminalia chebula* extract comprising a phytochemical selected from the group consisting of chebulagic acid, chebulinic acid, gallic acid, and a mixture thereof; and a compound of a metal selected from the group consisting of zinc, magnesium, calcium, and potassium;

wherein the reaction product comprises a salt, complex, or chelate of the phytochemical and the metal; and 25% to 67% by weight of a second ingredient comprising an extract of an herb selected from the group consisting of *Withania somnifera, Tinospora cordifolia* and *Andrographis paniculata,* wherein percentages of the first ingredient and the second ingredient are based on the combined weight of the first ingredient and the second ingredient; and wherein the first ingredient and the second ingredient act synergistically in a patient in need thereof to cause at least one of the following:

an increase in IL-2 production;

a decrease in IL-6 production;

an increase in interferon-γ production;

an increase in lymphocyte proliferation;

an increase in immune cell populations; and an increase in IgG production.

20. The herbal composition as claimed in claim 19, wherein:

the reaction product has a solubility of 1 gram in 10 to 20 mL water; and a 1% solution of the reaction product in water has a pH of 5.5 to 5.9.

* * * * *